(12) United States Patent
Zielinski et al.

(10) Patent No.: US 10,182,729 B2
(45) Date of Patent: Jan. 22, 2019

(54) SYSTEMS AND METHODS FOR MONITORING HEMODYNAMIC STATUS

(71) Applicant: Medtronic, Inc., Minneapolis, MN (US)

(72) Inventors: Todd M. Zielinski, Ham Lake, MN (US); David A. Anderson, Stanchfield, MN (US); Tom D. Bennett, Shoreview, MN (US); James K. Carney, Roseville, MN (US); Can Cinbis, Salt Lake City, UT (US); Yong K. Cho, Excelsior, MN (US); Jonathan L. Kuhn, Ham Lake, MN (US); Brian B. Lee, Golden Valley, MN (US); Richard J. O'Brien, Hugo, MN (US); Eduardo N. Warman, Maple Grove, MN (US); Vinod Sharma, Maple Grove, MN (US)

(73) Assignee: Medtronics, Inc., Minneapolis, MN (US)

( * ) Notice: Subject to any disclaimer, the term of this patent is extended or adjusted under 35 U.S.C. 154(b) by 0 days.

(21) Appl. No.: 15/253,229

(22) Filed: Aug. 31, 2016

(65) Prior Publication Data

US 2018/0055386 A1    Mar. 1, 2018

(51) Int. Cl.
| A61B 5/04 | (2006.01) |
| A61B 5/021 | (2006.01) |
| A61B 5/00 | (2006.01) |
| A61B 5/0205 | (2006.01) |
| A61B 5/026 | (2006.01) |

(Continued)

(52) U.S. Cl.
CPC ........ *A61B 5/02108* (2013.01); *A61B 5/0002* (2013.01); *A61B 5/0031* (2013.01); *A61B 5/021* (2013.01); *A61B 5/0205* (2013.01); *A61B 5/0261* (2013.01); *A61B 5/02125* (2013.01); *A61B 5/0402* (2013.01); *A61B 5/08* (2013.01); *A61B 5/686* (2013.01); *A61B 5/746* (2013.01)

(58) Field of Classification Search
CPC . A61B 5/02108; A61B 5/0002; A61B 5/0004; A61B 5/0006; A61B 5/0031; A61B 5/0205; A61B 5/021; A61B 5/02125; A61B 5/0261; A61B 5/0402; A61B 5/08; A61B 5/686; A61B 5/746
See application file for complete search history.

(56) References Cited

U.S. PATENT DOCUMENTS

| 8,147,416 | B2 | 4/2012 | Fayram et al. |
| 8,162,841 | B2 | 4/2012 | Keel et al. |
| 8,313,439 | B2 | 11/2012 | McCombie et al. |

(Continued)

OTHER PUBLICATIONS

Yano et al., "Nocturnal Blood Pressure, Morning Blood Pressure Surge, and Cerebrovascular Events," *Current Hypertension Reports*, Jun. 2012; 14(3):219-227. Available online Apr. 22, 2012.

(Continued)

*Primary Examiner* — George Manuel

(57) ABSTRACT

The exemplary systems and methods may monitor one or more signals to be used to assess the hemodynamic status of a patient. The one or more signals may be used to calculate, or determine, a plurality of pulse transit times. The plurality of pulse transit times may be used to determine hemodynamic status values that may be indicative of a patient's aggregate hemodynamic status.

21 Claims, 23 Drawing Sheets

(51) Int. Cl.
*A61B 5/0402* (2006.01)
*A61B 5/08* (2006.01)

(56) References Cited

U.S. PATENT DOCUMENTS

| | | | |
|---|---|---|---|
| 8,574,161 B2 | 11/2013 | Banet et al. | |
| 9,037,208 B2 | 5/2015 | Furman | |
| 9,408,542 B1 | 8/2016 | Kinast et al. | |
| 2004/0133081 A1* | 7/2004 | Teller | A61B 5/01 |
| | | | 600/300 |
| 2008/0183083 A1 | 7/2008 | Markowitz et al. | |
| 2009/0216132 A1 | 8/2009 | Orbach | |
| 2010/0160798 A1 | 6/2010 | Banet et al. | |
| 2011/0009754 A1 | 1/2011 | Wenzel et al. | |
| 2011/0224520 A1 | 9/2011 | Skerl et al. | |
| 2013/0041269 A1* | 2/2013 | Stahmann | A61B 5/686 |
| | | | 600/484 |
| 2014/0088385 A1* | 3/2014 | Moon | A61B 5/1118 |
| | | | 600/324 |
| 2014/0187941 A1 | 7/2014 | Shusterman | |
| 2014/0249398 A1 | 9/2014 | Morris et al. | |
| 2014/0276123 A1 | 9/2014 | Yang | |
| 2015/0051467 A1 | 2/2015 | Corbucci et al. | |
| 2015/0088216 A1 | 3/2015 | Gordon et al. | |
| 2017/0055845 A1* | 3/2017 | Mirov | A61B 5/0205 |

OTHER PUBLICATIONS (PCT/US2017/049537) PCT Notification of Transmittal of the International Search Report and the Written Opinion of the International Searching Authority, dated Nov. 9, 2017, 13 pages.

\* cited by examiner

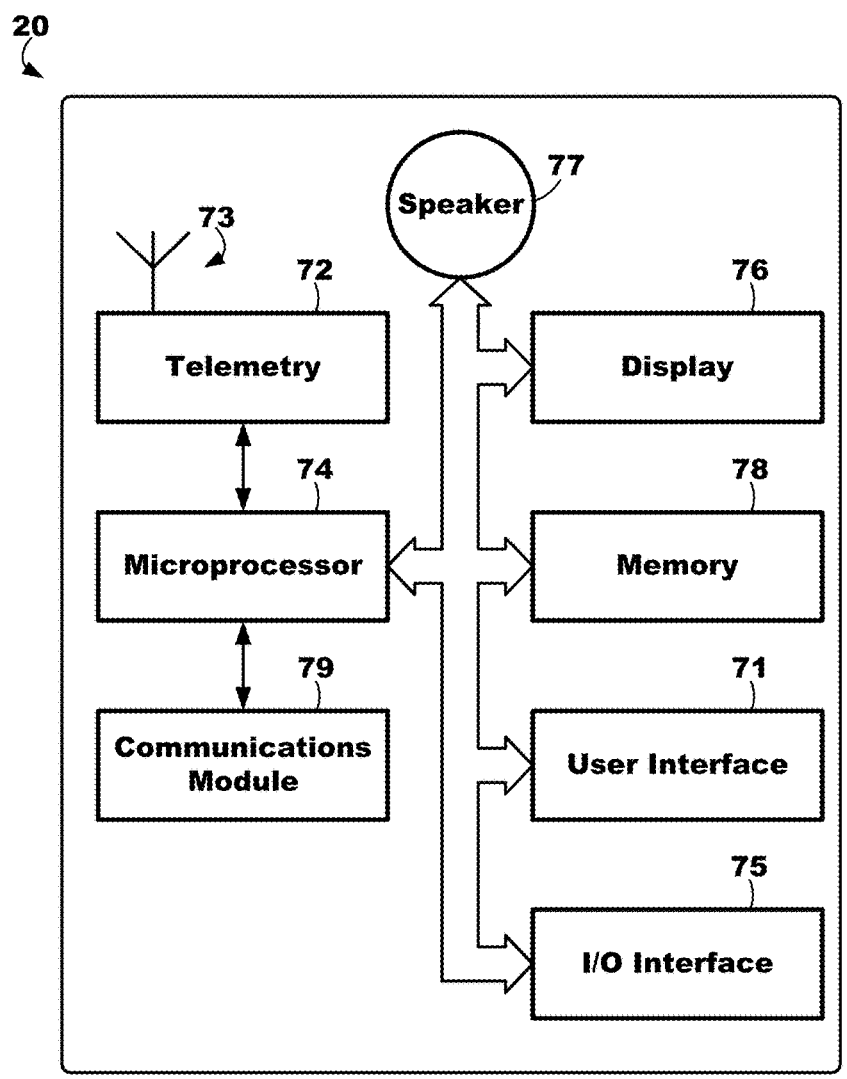

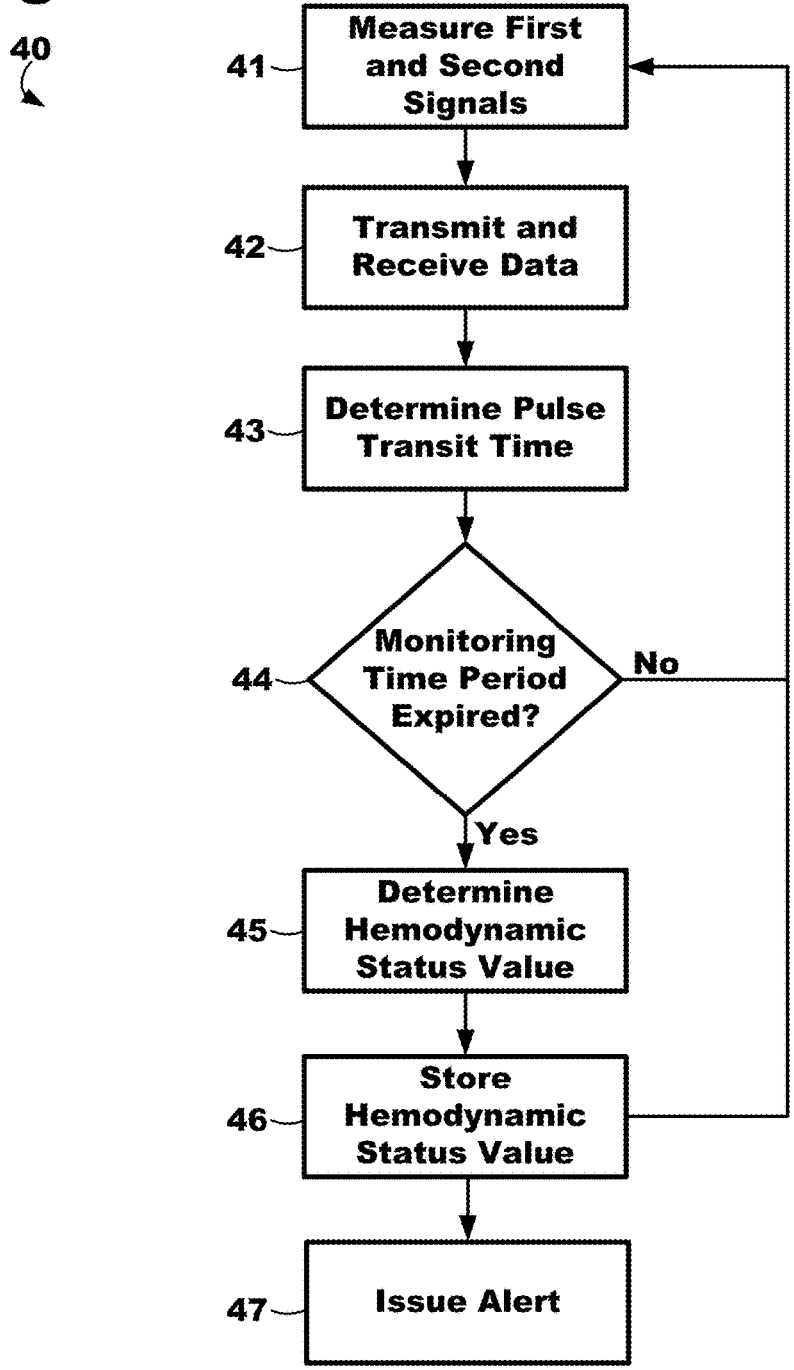

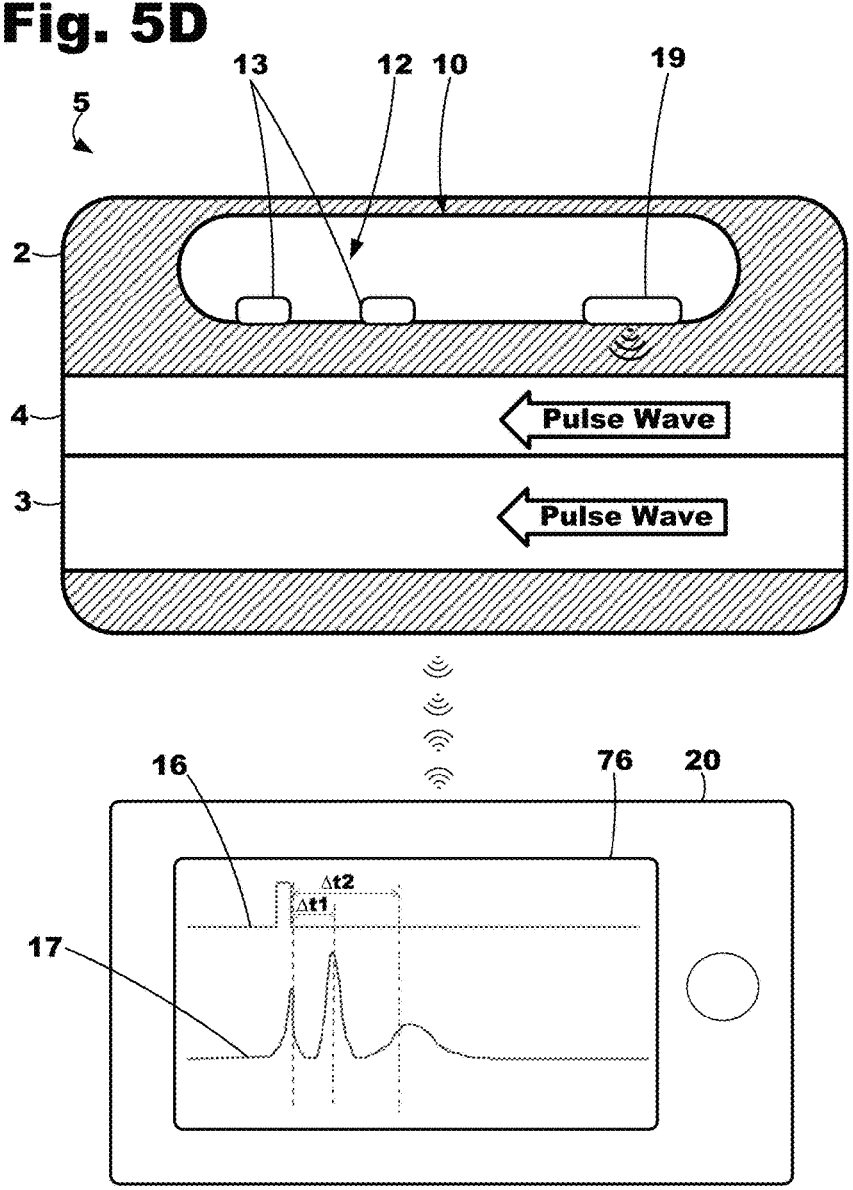

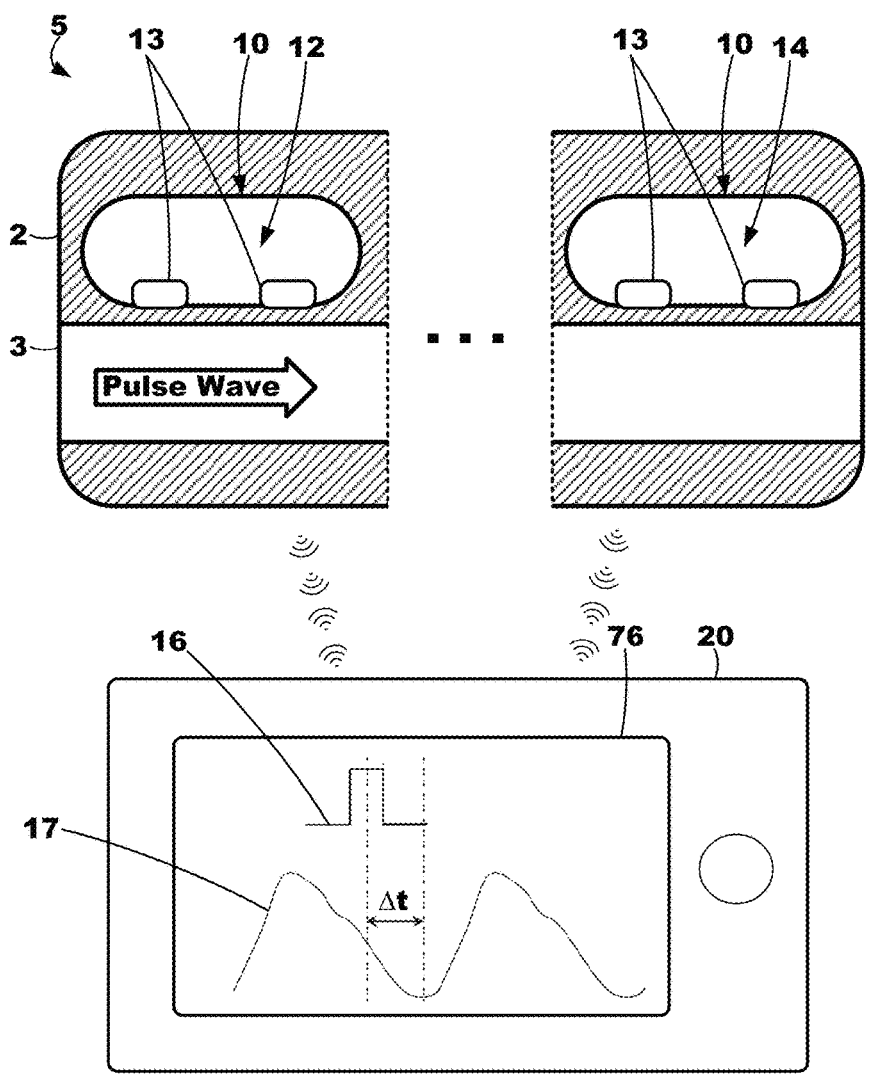

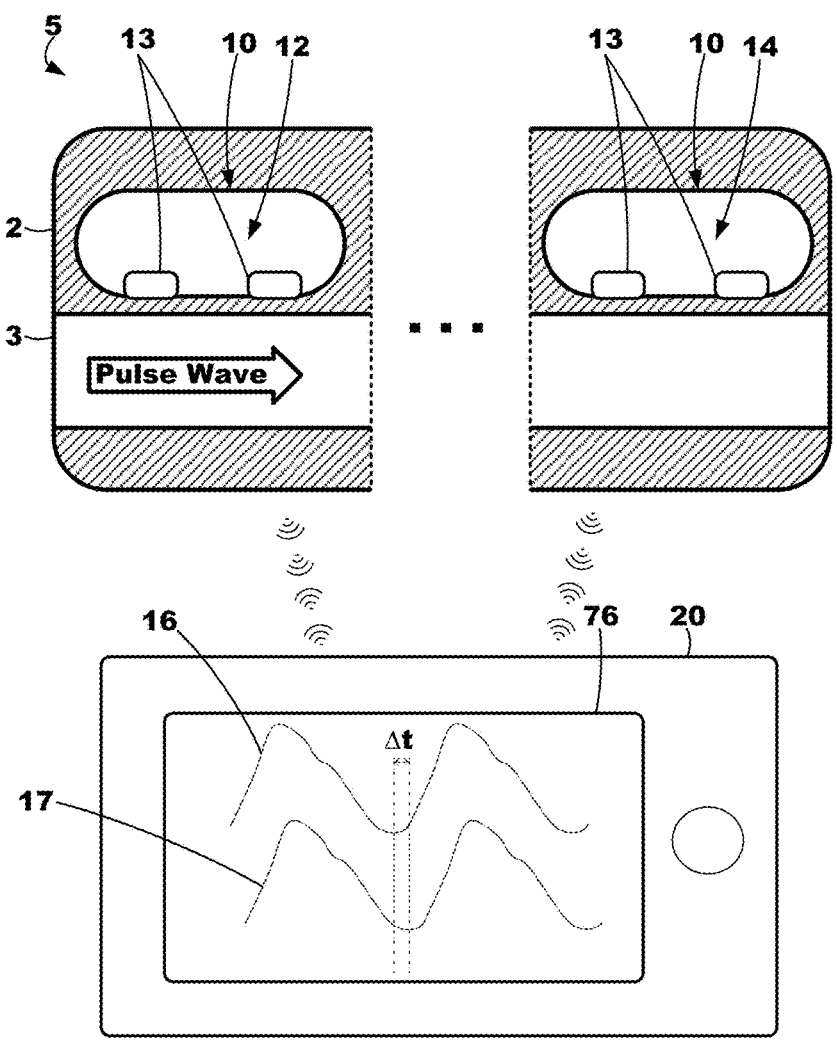

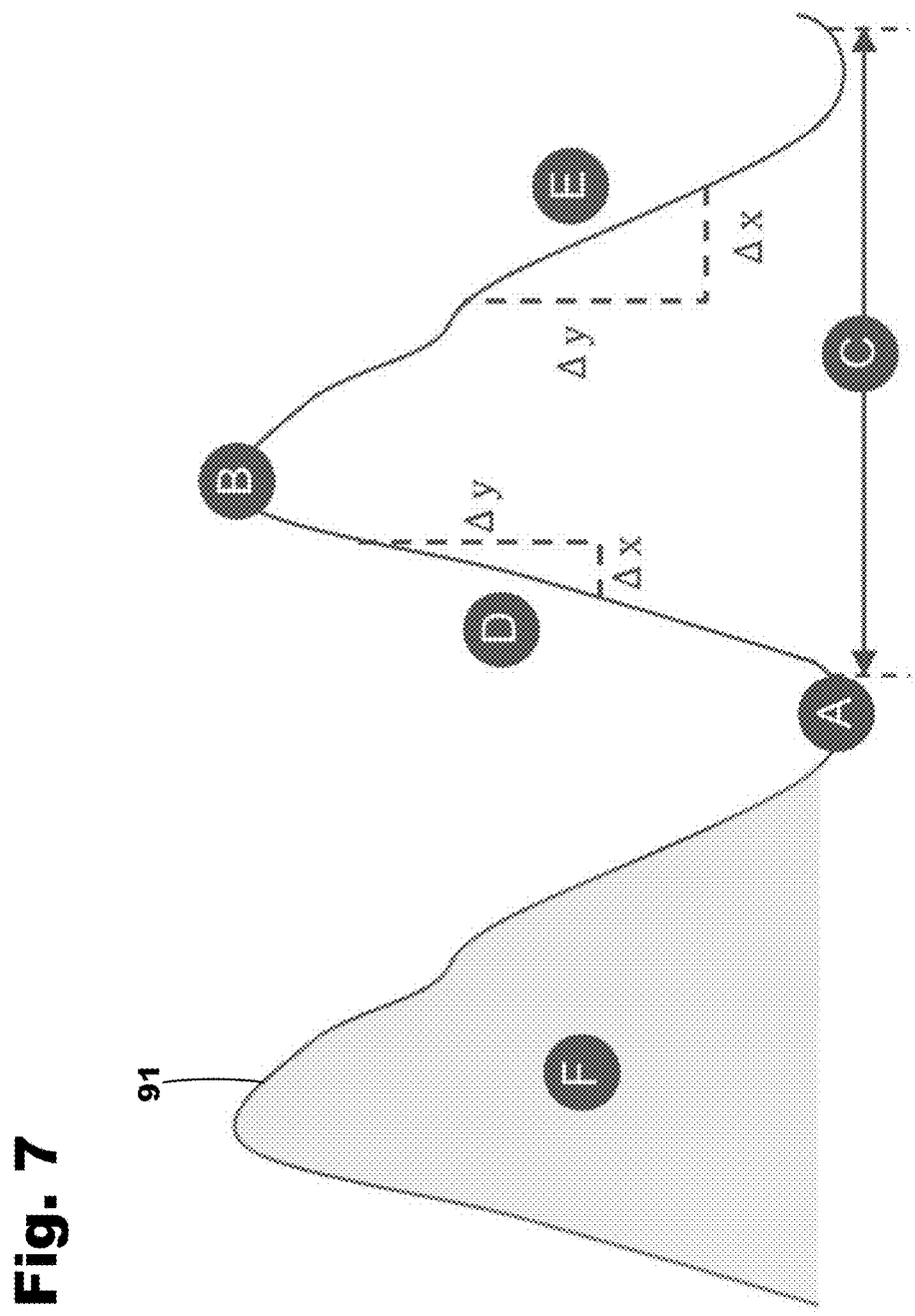

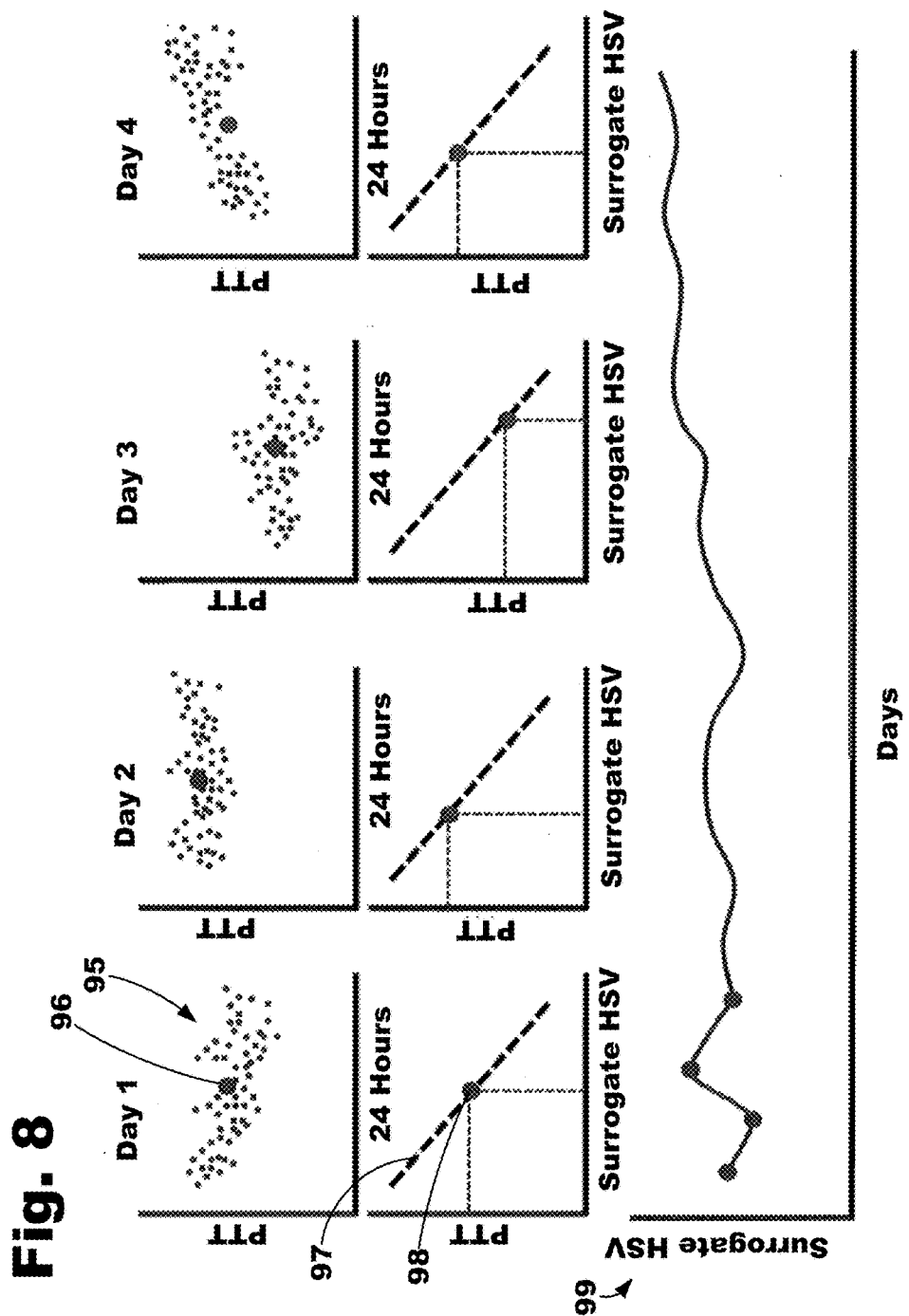

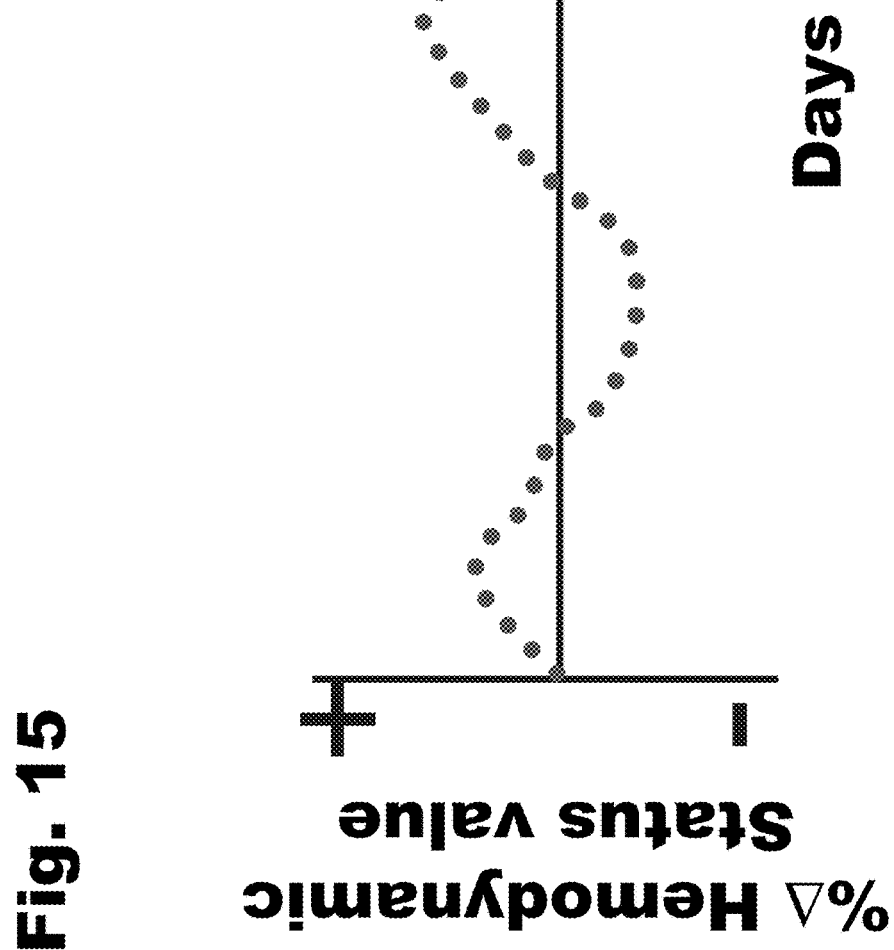

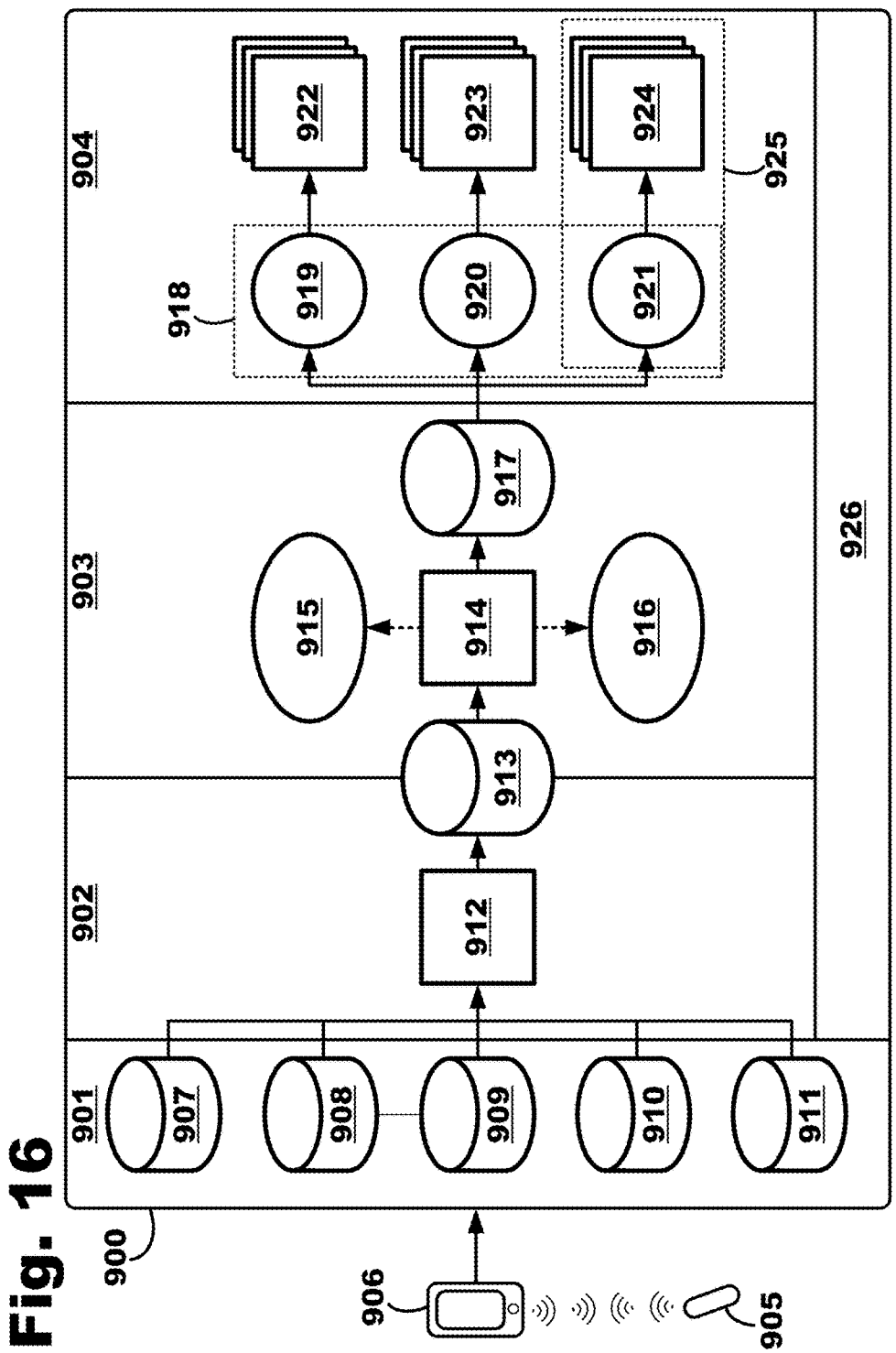

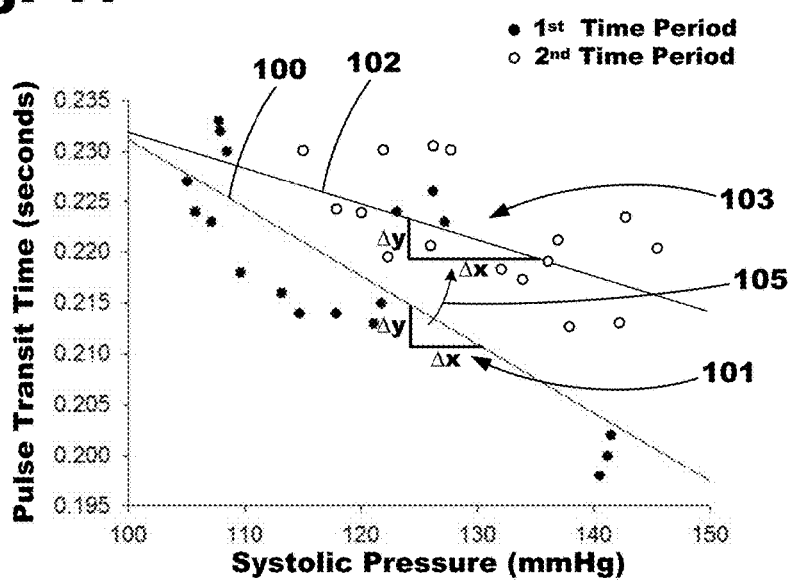

SYSTEMS AND METHODS FOR MONITORING HEMODYNAMIC STATUS

The present disclosure pertains to systems and methods for monitoring the hemodynamic status of patients using one or more devices (e.g., implantable devices) and an external monitoring device.

Blood pressure may increase with worsening heart failure. As blood pressure increases, blood vessel diameter may increase and blood vessels may become less compliant (e.g., stiffen). During clinical examination of heart failure patients, echocardiography can be used to monitor blood vessel diameter as an indicator of cardiac health.

SUMMARY

The exemplary systems and methods described herein may generally be described as monitoring at least two signals from tissue from a patient located in proximity to a blood vessel such as an artery. A first signal may be measured in tissue closer to the heart (e.g., closer to the heart along a circulator path) than the second signal. A fiducial point such as, e.g., a maximum peak value, etc., may be selected for each signal, and the time between the fiducial points in the signals may be determined, which is a pulse transit time. Pulse transit times may be periodically measured over a monitoring time period such as, e.g., half day, a whole day, nighttime, daytime, etc. The pulse transit times may then be analyzed to determine, or assess, the hemodynamic status of the patient. For example, a hemodynamic status value may be generated based on the pulse transit times measured during a monitoring time period. Thus, a hemodynamic status value may be generated for each monitoring time period, and the hemodynamic status values may be plotted over time such that a user to can view and analyze trends, the system may compare the hemodynamic status values to baseline values to generate alerts, etc. In one or more embodiments, the hemodynamic status value may be a surrogate aggregate blood pressure value.

The exemplary systems and methods may use one or more implantable devices (e.g., subcutaneously, paravascular devices) and/or one or more non-implantable devices to measure the at least two signals from the tissue of the patient and an external monitoring device. The one or more implantable and/or non-implantable devices may be wirelessly operably coupled to the external monitoring device to transfer data therebetween. In at least one embodiment, the one or more implantable and/or non-implantable devices may transfer a digital representation of the first and second signals to the external monitoring device such that external monitoring device can calculate a pulse transit time from the digital representation of the first and second signals. In at least one embodiment, the one or more implantable and/or non-implantable devices may transfer a time stamp representative of the time at which a fiducial point occurred in the first and second signals to the external monitoring device such that external monitoring device can calculate a pulse transit time from the time stamps. In at least one embodiment, an implantable and/or non-implantable devices may issue a pulse associated with a fiducial point in the first signal, and then transfer a time stamp representative of the time at which the pulse was delivered to the external monitoring device. Another implantable and/or non-implantable device may either transfer a digital representation of the second signal (which, e.g., may include the pulse) or a time stamp corresponding to when the pulse is sensed, or occurs, in the second signal to the external monitoring device such that external monitoring device can calculate a pulse transit time from the data.

One exemplary system for use in assessment of a patient's hemodynamic status may include one or more devices (e.g., implantable devices, subcutaneously implantable devices, etc.) and an external monitoring device. The one or more devices may include a first sensor to measure a first signal from tissue of a patient, and a second sensor to measure a second signal from tissue of the patient from a different location along a circulatory path from the patient's heart than the first sensor. The one or more devices may be configured to periodically measure the first and second signals over a monitoring time period (e.g., the monitoring time period is greater than or equal to 1 hour). The external monitoring device may be wirelessly operatively coupled to the one or more devices and configured to receive data representative of the first and second signals from the one or more devices and determine a pulse transit time based on the data representative of the first and second signals for each measurement of the first and second signals resulting in a plurality of pulse transit times for the monitoring time period. The external monitoring device may be further configured to determine a surrogate hemodynamic status value based on the plurality of pulse transit times representative of the patient's aggregate hemodynamic status for the monitoring time period.

One exemplary system for use in assessment of a patient's hemodynamic status may include one or more devices (e.g., implantable devices, subcutaneously implantable devices, etc.) and an external monitoring device. The one or more devices may include a first sensor to measure a first signal from tissue of a patient, and a second sensor to measure a second signal from tissue of the patient from a different location along a circulatory path from the patient's heart than the first sensor. The one or more devices may be configured to periodically measure the first and second signals over a monitoring time period (e.g., the monitoring time period is greater than or equal to 1 hour). The one or more devices may be further configured to determine a pulse transit time based on the data representative of the first and second signals for each measurement of the first and second signals resulting in a plurality of pulse transit times for the monitoring time period and determine a surrogate hemodynamic status value based on the plurality of pulse transit times representative of the patient's aggregate hemodynamic status for the monitoring time period. The external monitoring device may be wirelessly operatively coupled to the one or more devices and configured to receive the surrogate hemodynamic status value and/or data representative of the first and second signals from the one or more devices.

One exemplary method for use in assessing a patient's hemodynamic status may include periodically measuring a first signal from tissue of a patient and a second signal from tissue of the patient in a different location along a circulatory path from the patient's heart than where the first signal is measured over a monitoring time period (e.g., the monitoring time period may be greater than or equal to 1 hour), receiving data representative of the first and second signals using an external monitoring device, determining a pulse transit time based on the data representative of the first and second signals for each measurement of the first and second signals resulting in a plurality of pulse transit times for the monitoring time period, and determining a hemodynamic status value based on the plurality of pulse transit times representative of the patient's aggregate hemodynamic status for the monitoring time period.

One exemplary system for use in assessment of a patient's hemodynamic status may include one or more devices (e.g., implantable devices, subcutaneously implantable devices, etc.) and an external monitoring device. The one or more devices may include a pulse generator to generate a pulse in tissue of a patient and a sensor to measure a signal from tissue of the patient from a different location along a circulatory path from the patient's heart than the pulse generator. The one or more devices may be configured to periodically deliver a pulse and measure the signal over a monitoring time period. The external monitoring device may be wirelessly operatively coupled to the one or more devices and configured to receive a time stamp corresponding to the delivery of the pulse and data representative of the signal from the one or more devices, and determine a pulse transit time based on the time stamp and the data representative of the signal for each pulse delivery and measurement of the signal resulting in a plurality of pulse transit times for the monitoring time period. The external monitoring device may be further configured to determine a surrogate hemodynamic status value based on the plurality of pulse transit times representative of the patient's hemodynamic status for the monitoring time period.

In one or more embodiments, the external monitoring device may be further configured to execute or the method further includes monitoring the hemodynamic status values for a plurality of monitoring time periods and determining whether the hemodynamic status of the patient has changed based on the hemodynamic status values over the plurality of monitoring time periods. Further, an alert may be issued if the hemodynamic status of the patient has changed based on the hemodynamic status values.

In one or more embodiments, the external monitoring device may be further configured to execute or the method further includes receiving a plurality of blood pressure values of the patient synchronized to the plurality of pulse transit times over the monitoring time period, modelling a relationship between the plurality of blood pressure values and the plurality of pulse transit times, monitoring the relationship between the plurality of blood pressure values and the plurality of pulse transit times for at least two monitoring time periods, and determining whether the hemodynamic status of the patient has changed based on a change in the relationship between the plurality of blood pressure values and the plurality of pulse transit times over the at least two monitoring time periods.

In one or more embodiments, the one or more devices may include a first device including the first sensor and a second device including the second sensor. In one or more embodiments, the one or more devices may include a single implantable device including the first sensor and the second sensor.

In one or more embodiments, the first signal may include one or more of an electrocardiography signal and an impedance signal. Further, in at least one embodiment, the data representative of the first signal may include a digital representation of one of an electrocardiography signal, an impedance signal, an acoustic signal, an optical signal, and an accelerometer signal. Still further, in at least one embodiment, the data representative of the first signal may include a time stamp corresponding to a fiducial point within one of an electrocardiography signal, an impedance signal, an optical signal sensed, an acoustic signal, and an accelerometer signal.

In one or more embodiments, the second signal may include one or more of an impedance signal sensed, an optical signal sensed, an acoustic signal sensed, and an accelerometer signal.

One exemplary system for use in assessment of a patient's hemodynamic status may include one or more devices (e.g., implantable devices, subcutaneously implantable devices, etc.) and an external monitoring device. The one or more devices may include a first sensor to measure a first signal from tissue of a patient, and a second sensor to measure a second signal from tissue of the patient from a different location along a circulatory path from the patient's heart than the first sensor. The one or more devices may be configured to periodically measure the first and second signals over a first monitoring time period and a second monitoring time period (e.g., the monitoring time periods may be greater than or equal to 1 hour). The external monitoring device may be wirelessly operatively coupled to the one or more devices and configured to receive data representative of the first and second signals from the one or more devices and determine a pulse transit time based on the data representative of the first and second signals for each measurement of the first and second signals resulting in a plurality of pulse transit times for the first and second monitoring time periods. The external monitoring device may be further configured to receive a plurality of blood pressure values of the patient synchronized to the plurality of pulse transit times over at least the first monitoring time period and the second monitoring time period, generate a pulse transit time-blood pressure relationship between the plurality of pulse transit times and the plurality of blood pressure values and for each of the first monitoring time period and the second monitoring time period, and determine whether the hemodynamic status of the patient has changed based on a change in the pulse transit time-blood pressure relationship over the first and the second monitoring time periods.

One exemplary method for use in assessing a patient's hemodynamic status may include receiving a plurality of pulse transit times of a patient over at least a first monitoring time period and a second monitoring time period, receiving a plurality of blood pressure values of the patient synchronized to the plurality of pulse transit times over at least the first monitoring time period and the second monitoring time period, generating a pulse transit time-blood pressure relationship between the plurality of pulse transit times and the plurality of blood pressure values and for each of the first monitoring time period and the second monitoring time period, and determining whether the hemodynamic status of the patient has changed based on a change in the pulse transit time-blood pressure relationship over the first and the second monitoring time periods.

One exemplary system may include a plurality of implantable and/or non-implantable devices to measure sensed waveforms to determine hemodynamic status. The system may be configured to measure a primary signal on a device located in a specific anatomical region of the body and measure a secondary signal on a second device or plurality of devices located in different anatomical regions of the body. The primary signal may include sensed waveform parameter(s) associated with the cardiac and/or respiratory cycle. The secondary signal may include a sensed waveform(s) or timing interval(s) associated with the primary signals sensed waveform relative to a cardiac and/or respiratory cycle. Both signals can be measured with a device electrode array placed in the subcutaneous tissue in close proximity to the heart, artery, vein, and/or capillary bed, within the heart, artery, vein, and/or capillary bed, or combination thereof. Waveform fiducial points and timing intervals can be measured and compared between the primary and secondary signals. Communication between the devices may include direct radio-frequency tissue communication schemes or other communication schemes utilizing an external device as a central hub (such as a cell phone) for independent communication with the implanted devices and subsequent data transmission to a call center or health care provider.

One exemplary system may include a plurality of devices to measure a pulsed timing signal and a sensed waveform to determine hemodynamic status. The system may be configured to monitor a primary signal on a device located in a specific anatomical region of the body. The primary signal may include sensed waveform parameter(s) associated with the cardiac and/or respiratory cycle (e.g., R-wave in an electrocardiogram). A subsequent pulse associated with the timing of the aforementioned sensed waveform(s) may be transmitted to a secondary device or plurality of devices. The secondary device or plurality of devices located in different anatomical regions of the body can sense the primary devices transmitted pulsed signal and use the pulsed signal to perform an action or use the pulsed signal as a timing reference or time stamp. The secondary signal may include sensed waveform(s) and/or timing interval(s) associated with the primary signals pulsed timing waveform relative to a cardiac and/or respiratory event sensed by the primary device. Both signals can be measured with a device electrode array placed in the subcutaneous tissue in close proximity to the heart, artery, vein, and/or capillary bed, within the heart, artery, vein, and/or capillary bed, or combination thereof. Waveform fiducial points and timing intervals can be measured and compared between the primary and secondary signals or between the primary devices pulsed timing signal and the secondary signals. Communication between the devices may include direct radio-frequency tissue communication schemes or other communication schemes utilizing an external device as a central hub (such as a cell phone) for independent communication with the implanted devices and subsequent data transmission to a call center or health care provider.

One exemplary embodiment may include a single device to measure hemodynamic status. The system may be configured to monitor a primary signal on the single device located in a specific anatomical region of the body. The primary signal may include sensed waveform parameter(s) associated with the cardiac and/or respiratory cycle. A secondary signal may also be measured on the same device. The secondary signal may include sensed waveform(s) or timing interval(s) associated with the primary signals sensed waveform relative to a cardiac and/or respiratory cycle. Both signals can be measured with a device electrode array placed in the subcutaneous tissue in close proximity to the heart, artery, vein, and/or capillary bed, within the heart, artery, vein, and/or capillary bed, or combination thereof. Waveform fiducial points and timing intervals can be measured and compared between the primary and secondary signals. Communication between the device and an external device (such as a cell phone) may be used for data transmission to a call center or health care provider.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 3 is a functional block diagram of the exemplary external monitoring device of FIGS. 1A-1C.

FIG. 4 is a flow diagram of an exemplary method of monitoring hemodynamic status of a patient using, e.g., the systems and devices of FIGS. 1-3.

FIGS. 5C-5D depict exemplary systems for monitoring hemodynamic status of a patient including a single implantable device having one sensor and one pulse generator.

FIGS. 6A-6C depict exemplary systems for monitoring hemodynamic status of a patient including a two implantable devices.

FIG. 7 is a graph of exemplary arterial waveforms over time including a plurality of selected fiducial points for use with the exemplary systems and methods of FIGS. 1-6.

FIG. 8 depicts a plurality of graphs showing how a plurality of pulse transit times may be converted into a surrogate hemodynamic status value and plotted over time.

FIG. 15 is a graph of exemplary change in hemodynamic status value over time determined using, e.g., the exemplary systems and methods of FIGS. 1-6.

FIG. 16 is a block diagram of a centralized data system for use the exemplary systems and methods of FIGS. 1-6.

FIG. 17 is a graph of pulse transit time data versus systolic blood pressure measured during a first time period and a second time period.

DETAILED DESCRIPTION OF EXEMPLARY EMBODIMENTS

Figure 1A:
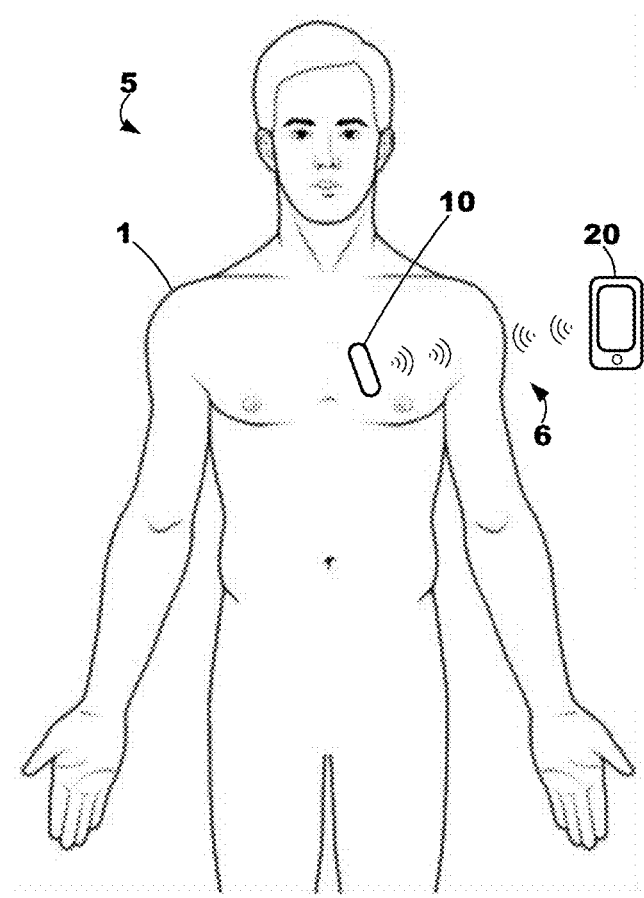
FIG. 1A depicts an exemplary system for monitoring hemodynamic status of a patient including a single implantable device implanted proximate the patient's heart and an external monitoring device.

Exemplary methods, apparatus, and systems shall be described with reference to FIGS. 1-17. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The human arterial system can be associated with a vast array of distensible tubes (e.g., blood vessels such as arteries capillaries), designed to distribute blood volume throughout the body. A blood volume impulse generated by the heart distributes a blood volume pulse along the system of tubes at a velocity which is determined by the properties of the tube and the fluid contained within. The principal property of the tube can be associated with vessel stiffness and the velocity of the generated pulse traveling through the system of tubes. Stiffness of the arterial vasculature is directly associated with the pressure measured within the artery. The Moens-Korteweg equation defines the velocity of the propagating pulse as pulse wave velocity (PWV) as follows:

$$PWV = \sqrt{\frac{Eh}{2r\rho}}$$

where E is Young's modulus of the arterial wall that defines the elastic properties of the arterial wall per unit area, h/2r is the arterial wall thickness divided by the arterial diameter, and $\rho$ is the density of blood.

Similar to pulse wave velocity is pulse transit time (PTT). Pulse transit time may generally described as the time it takes for a pressure or flow wave to propagate between two arterial sites. Daily variation in blood pressure and associated variation in pulse transit time may occur naturally as the body adjusts blood volume distribution to the body by regulation of vasoconstriction and vasodilation properties of arterial vessels. This variation can be related to changes in autonomic tone due to activity, diet, medication, stress, anxiety, sleeping and the like. The exemplary systems, devices, and methods described herein may account for this naturally occurring variation in blood pressure and associated pulse transit time to, e.g., provide a hemodynamic status of a patient. For example, the exemplary systems, devices, and methods described herein may be described as calculating a statistical parameter that represents a surrogate hemodynamic status value from a plurality of pulse transit times sensed over a predetermined data collection period. The processes of calculating a surrogate hemodynamic status value from the plurality pulse transit times may account for the continuous variation in blood pressure.

Sensor waveforms (e.g., impedance waveforms, optical waveforms, etc.) measured cutaneously, subcutaneously, intravascular, paravascular, intracardiac, or a combination thereof may contain a high frequency cardiac component superimposed on a low frequency respiratory component and a DC or mean component. Each of these components may have clinical diagnostic utility. For example, the high frequency cardiac component may provide indicators of cardiac or hemodynamic function. Further, for example, the low frequency component may provide indicators of respiratory rate and lung compliance. Still further, for example, the DC or mean component may provide an indicator of patient fluid status.

Applications for diagnostic monitoring may have overlapping cardiovascular disease specific indications for use as a potential surrogate to measure cardiac function and/or blood flow or global fluid status. For example, hypertension may be a precursor to, or aggravating factor for, heart failure. A variety of cardiovascular pressures, e.g., intracardiac, arterial, and venous pressures, etc., may also be used as indicators of the progression of maladies such as heart failure and hypertension as well as the hemodynamic status of patient in general, although methods to measure the aforementioned parameters may often use invasive sensor techniques. The exemplary systems, devices, and methods described herein may be described as using less invasive sensor measurement methods, which may be useful to monitor asymptomatic chronic diseases such as, e.g., hypertension.

Chronic methods to monitor relative cardiac function and/or blood flow using implantable and/or non-implantable sensors as a relative hemodynamic surrogate may provide clinical utility for monitoring the onset and progression or regression of cardiovascular disease based on sensor measurement algorithms that can determine relative cardiovascular parameters by measurement of waveform specific fiducial parameters or time duration measurements between fiducial waveform parameters and/or sensed and/or device pulsed waveforms relative to time points specific to the cardiac and/or respiratory cycles. In one such example, pulse transit time calculation methods may be used. Pulse transit time may be generally described as the time it takes a pulsation (e.g., pressure pulsation) to travel between two blood vessel (e.g., arterial) sites, one of such sites located further along a circulatory path from the heart than the other such site. For example, the interval between the peak of the R-wave on an electrocardiogram and the onset of the corresponding pressure pulse at a distal anatomical location (e.g., distal along a circulatory path) may be used for pulse transit time. Pulse transit times and/or one or more values derived therefrom such as a hemodynamic status values as described herein may be a valuable metric for chronic hemodynamic monitoring of a patient.

Multiple electrode vector configurations may be used, or selected to be used, to measure pulse transit time as described herein. Electrode configurations may include electrodes isolated to a specific device or electrodes in combination with a plurality of devices to detect sensed or pulsed waveforms.

This disclosure herein describes methods for detecting changes in a patient's hemodynamic status in healthy patients or unhealthy patients (e.g., cardiovascular, disease, etc.). Further, this disclosure further describes the use of a single implantable device or plurality of devices implanted in subcutaneous tissue in various anatomical locations. Diagnostic applications using the exemplary methods and devices may include monitoring cardiac function, cardiac anomalies, respiratory rate, respiratory anomalies, thoracic and peripheral limb fluid shifts, circadian fluid shift variation, etc.

In one or more exemplary embodiments, an implantable medical device or a plurality of devices (e.g., implantable, wearable, etc.) may monitor sensor values of an electric, optical, or acoustic field path that is between sensors that traverse the heart, a blood vessel, and/or capillary bed, within the heart, a blood vessel, and/or capillary bed, and next to the heart, a blood vessel, and/or capillary bed. It may be described that the sensed signal of such a path may be correlated with and varies in substantially the same manner as the blood flow within a vessel or capillary bed and/or various hemodynamic parameters associated with the cardiac or respiratory cycles. Thus, the sensed signal of the electric, optical, or acoustic field path may be monitored as a surrogate for cardiac function or flow in a vessel or capillary bed, and variations in the signal over time may indicate changes in hemodynamic performance in a manner analogous to conventional techniques used to identify changes to hemodynamic performance. Further, the signal may be also be described as an index of cardiac function, vessel distensibility, or vessel compliance.

Sensor values of an electric, optical, or acoustic field path may define a periodic function, e.g., waveform. The period of the periodic function may be correlated with the cardiac cycle and heart rate of a patient in much the same manner that a cardiovascular pressure waveform defines a periodic function. The exemplary systems described herein including one or more devices may monitor changes in the arterial and/or venous waveform over a number of periods. For example, the device or plurality of devices may compare a sensed or pulsed signal of a first period or a referenced time point to a sensed signal of a subsequent period. Further, the exemplary device or devices may also compare a range (corresponding to magnitude or time differences in waveform fiducial points) of a first period or referenced time point to a range of subsequent periods. Still further, the exemplary device or devices may also compare a range of sensor values measured between the heart or artery and the corresponding vein or capillary bed of a first period to a range of a subsequent period. Regardless, in one or more embodiments, the exemplary device or devices may determine whether the hemodynamic status of the patient has changed based on a daily, weekly, etc. basis based on comparisons between monitoring periods covering the day and night, or combinations thereof.

It may be further described that the exemplary systems may be configured to determine various conditions related to cardiovascular performance of the patient. For example, the exemplary systems may determine a change in hemodynamic performance, stroke volume, peripheral fluid accumulation, afterload, systolic function, or other characteristics of cardiovascular performance. In some examples, the one or more devices (e.g., implanted devices, wearable devices, etc.) may be communicatively coupled to another medical device or an independent external device, which may receive pulse transit time-related data from the devices, start or stop a measured timing intervals, trigger or send an alerts in response to a determined change in cardiovascular performance, etc.

Moreover, the exemplary one or more devices may use a combination of sensor technologies such as electrical (e.g., electrocardiogram, impedance, etc.), optical, pressure, or acoustic processes to measure waveform fiducial time points and/or time intervals between fiducial time points associated with the cardiac and/or respiratory cycles.

Figure 1B:
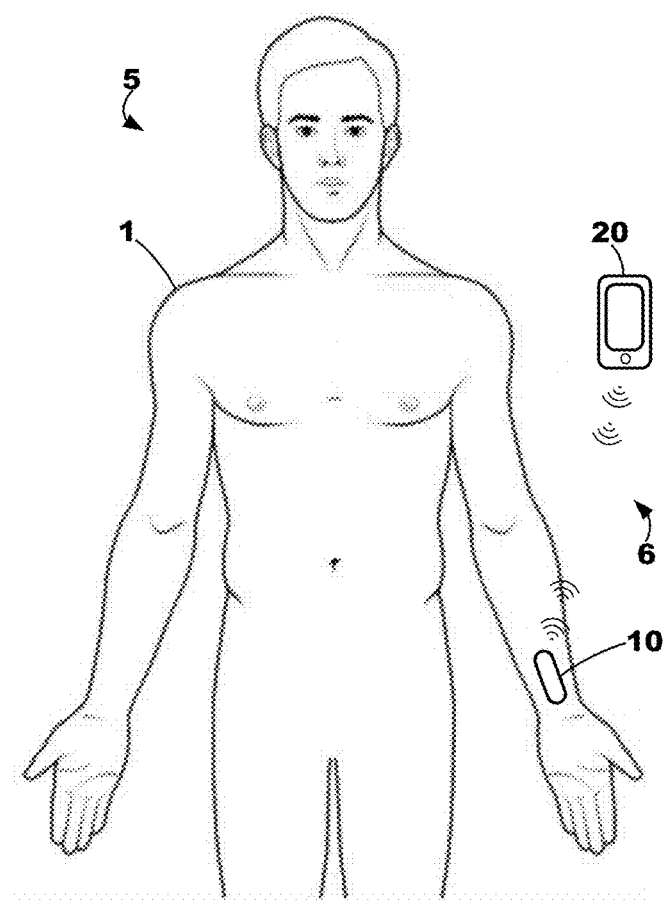
FIG. 1B depicts an exemplary system for monitoring hemodynamic status of a patient including a single implantable device implanted away from the patient's heart in the patient's arm and an external monitoring device.
Figure 1C:
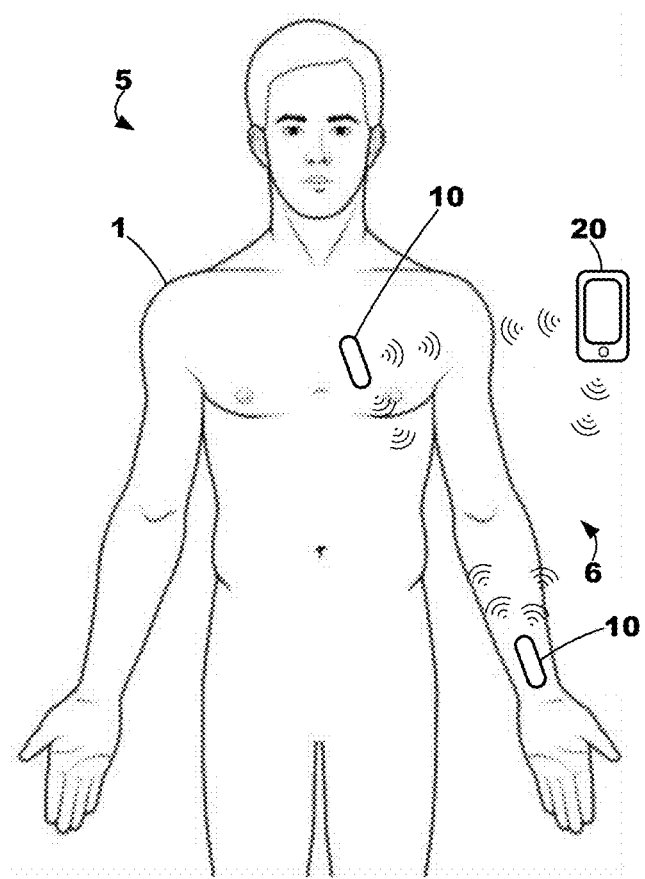
FIG. 1C depicts an exemplary system for monitoring hemodynamic status of a patient including two implantable devices and an external monitoring device.

As described herein, the exemplary systems and methods described herein may include or use one or more implantable and/or non-implantable devices for monitoring one or more signals to determine pulse transit times for using in assessing a patient's hemodynamic status. Exemplary systems 5 including one or more implantable devices 10 and an external monitoring device 20 are depicted in FIGS. 1A-1C. Although only implantable devices 10 are depicted in FIGS. 1A-1C, it is be understood that non-implantable devices may also be used to perform the same or similar functionality as described further herein. The implantable devices 10 will be described in further detail herein with respect to FIG. 2 and the external monitoring device 20 will be described in further detail herein with respect to FIG. 3.

An exemplary system 5 including a single implantable device 10 implanted proximate the heart of a patient 1 and an external monitoring device 20 is depicted in FIG. 1A. The implantable device 10 may be implanted in subcutaneous tissue in close proximity to, or within, the heart, an artery, a vein, arterial capillary bed, venous capillary bed, or combination thereof. For example, the implantable device 10 may be described as being implanted paravascular in proximity to an artery (e.g., located in the chest proximate the heart) so as to be able to monitor two or more signals from tissue proximate the artery. As will be described further herein, the single implantable device 10 may include at least two sensors, e.g., so as to be able to monitor two signals for the calculation, or determination, of pulse transit times. Further, one of the at least two sensors may be described as being further along a circulatory path from the patient's heart than the other sensor so as to, e.g., monitor signals for the calculation, or determination, of pulse transit times.

The implantable device 10 may further be wirelessly operably coupled to the external monitoring device 20 via a wireless channel 6 as indicated by the waveform symbols extending between the devices 10, 20. The wireless operable coupling 6 between the implantable device 10 and the external monitoring device 20 may allow data to be transferred between the two devices 10, 20 such as, e.g., measurement initiation signals, time synchronization signals, signal data, data representative of signal data, pulse transit times, any data usable to determine pulse transit time, waveforms, waveform digital representations, analog waveforms, etc. The implantable device 10 and the external monitoring device 20 may be continuously or intermittingly wirelessly coupled for data transfer therebetween. For example, data may flow continuously between the two devices 10, 20 or data may be exchanged, or transferred, between the two devices 10, 20 at selected intervals or whenever the devices 10, 20 come within a particular range of each other. In at least one embodiment, data is downloaded from the implantable device 10 to the external monitoring device 20 once a day.

An exemplary system 5 including a single implantable device 10 implanted away from the heart of a patient 1 in the patient's arm and an external monitoring device 20 is depicted in FIG. 1B. The implantable device 10 may be implanted in subcutaneous tissue in close proximity to an artery, a vein, arterial capillary bed, venous capillary bed, or combination thereof. For example, the implantable device 10 may be described as being implanted paravascular in proximity to an artery in the patient's 1 arm so as to be able to monitor two or more signals from tissue proximate the artery. As will be described further herein, the single implantable device 10 may include at least two sensors, e.g., so as to be able to monitor two signals for the calculation, or determination, of pulse transit times. Further, one of the at least two sensors may be described as being further along a circulatory path from the patient's heart than the other sensor so as to, e.g., monitor signals for the calculation, or determination, of pulse transit times. The implantable device 10 and the external monitoring device 20 of FIG. 1B may be wirelessly operably coupled in a similar manner as the implantable device 10 and the external monitoring device 20 of FIG. 1A.

An exemplary system 5 including two implantable device 10 and an external monitoring device 20 is depicted in FIG. 1C. One implantable device 10 is implanted in the same, or similar location, to the implantable device 10 shown in FIG. 1A, and the other implantable device 10 is implanted in the same, or similar location, to the implantable device 10 shown in FIG. 1B. As will be described further herein, each of the implantable devices 10 of FIG. 1C may include at least one sensor, e.g., so as to be able to monitor at least one signal for the calculation, or determination, of a pulse transit time. Further, a sensor of the device 10 located in the arm of the patient may be described as being further along a circulatory path from the patient's heart than the sensor of the device 10 in the patient's torso so as to, e.g., monitor signals for the calculation, or determination, of pulse transit times. Each of the implantable devices 10 and the external monitoring device 20 of FIG. 1C may be wirelessly operably coupled in a similar manner as the implantable device 10 and the external monitoring device 20 of FIG. 1A.

Figure 2:
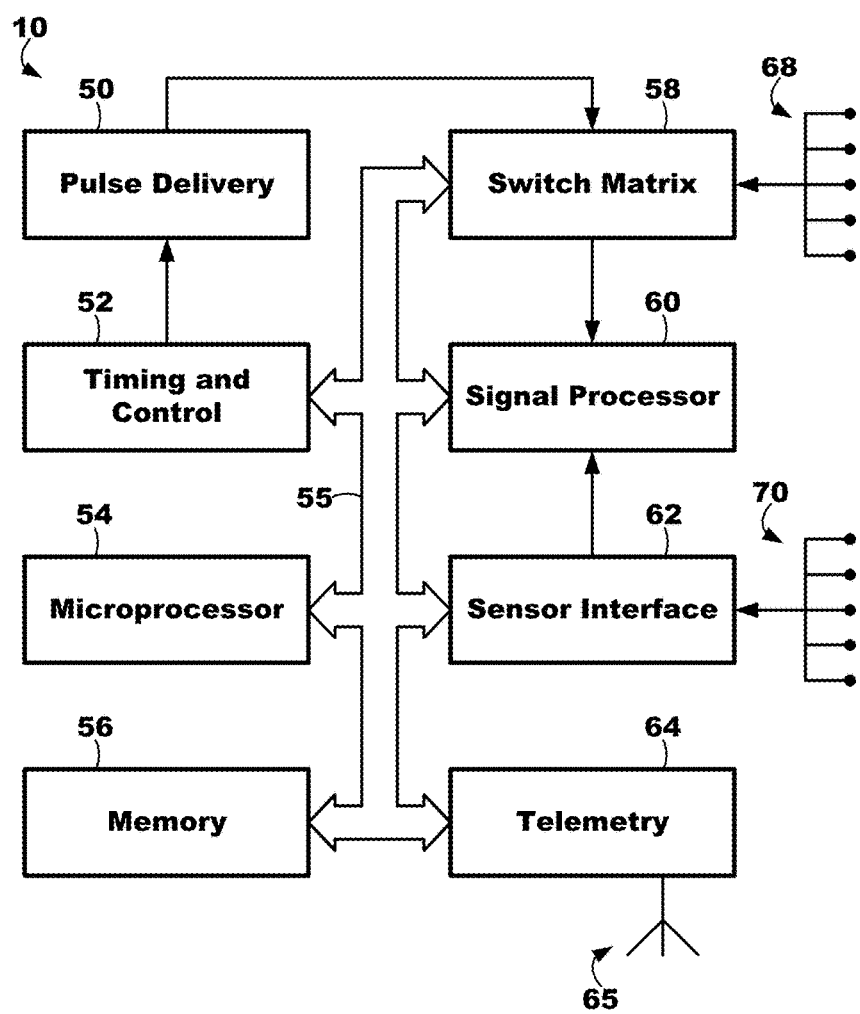
FIG. 2 is a functional block diagram of the exemplary implantable devices of FIGS. 1A-1C.

FIG. 2 is a functional block diagram of the exemplary implantable devices 10 shown in FIGS. 1A-1C. The exemplary implantable devices 10 may generally include an operating system that may employ microprocessor 54 to control device functions. The microprocessor 54 and associated memory 56 may be coupled to the various components of device 10 via a data/address bus 55.

The devices 10 may include electrodes 68 used for at least sensing electrical signals within the body such as, e.g., cardiac signals (e.g., electrocardiogram signals), impedance values, and/or any electrical signal associated with a physiological parameter for use in pulse transit time calculation or measurement. The electrical signals may be measured, or sensed, from any tissue (e.g., a tissue bed) where a hemodynamic pulse is observable (e.g., subcutaneously paravascular, etc.). In at least one embodiment, the electrodes 68 may be used to measure cardiac signals, impedance values, and/or any electrical signal associated with a physiological parameter from tissue proximate a blood vessel (e.g., arterial tissue, venous tissue, etc.). The electrodes 68 used for sensing and electrodes used for stimulation may be selected via a switch matrix 58. When used for sensing, electrodes 68 are coupled to a signal processor, or processing circuitry, 60 via the switch matrix 58. The signal processor, or processing circuitry, 60 may include sense amplifiers and may include other signal conditioning circuitry and an analog-to-digital converter. In essence, the device 10 may include a sensing module, e.g., that includes switch matrix 58, signal processing circuitry 60, etc. for monitoring one or more signals that may be used by microprocessor 54 or transmitted to another device such as, e.g., the external monitoring device 20, for use in determining pulse transit times, in determining a patient's hemodynamic status (e.g., chronic hemodynamic status), etc.

The device 10 may further include one or more additional sensors 70 such as pressure sensors, accelerometers, flow sensors, blood chemistry sensors, activity sensors, acoustic sensors, posture sensors, respiration sensors, etc. that may be used for the determination, or calculation, of pulse transit time. The sensors 70 may be coupled to the remainder of the device 10 via a sensor interface 62 which provides sensor signals to signal processing circuitry 60. Signals monitored, or measured, using the additional sensors 70 may be used by microprocessor 54 or transmitted to another device such as, e.g., the external monitoring device 20, for use in determining pulse transit times, in determining a patient's hemodynamic status (e.g., chronic hemodynamic status), etc.

The device 10 may further include pulse delivery module 50 for delivering pulses, such as electrical stimulations/pulses under the control of timing and control circuitry 52 for use in measuring pulse transit times. The pulse delivery module 50 may include various apparatus configured to deliver pulses such as, e.g., electrical pulses (e.g., to contract tissue to cause a pressure pulse within a blood vessel or vasculature, etc.), pressure pulses, acoustic pulses, ultrasound pulses, etc., to a patient's tissue. Generally, the pulse deliver module 50 may be described as being configured to deliver, or initiate, mechanical, or physical, pulses to a patient's blood vessel (e.g., an artery or a vein). The pulse delivery module 50 may include a pulse-generating circuitry for generating therapeutic electrical stimulation pulses (e.g., bursts of electrical stimulation pulses) under the control of timing and control circuitry 52. The pulse delivery module 50 may be further coupled to two or more electrodes 68 via a switch matrix 58 that is used for selecting which electrodes and corresponding polarities are used for delivering electrical pulses.

As described herein, the device 10 includes memory 56 for storing a variety of processes and methods used to drive the operation of the device 10. The memory 56 may also be used for storing data, e.g., data monitored using the electrodes 68 and sensors 70, intermediate data or other values (e.g., time stamps, etc.) calculated or determined by the microprocessor 54 based on sensor data, data compiled from sensed signals and/or relating to device operating history (e.g., for use in delivering, adjusting, controlling, initiating, and/or terminating pulses), and/or data for communicating such data outside of the patient (e.g., using telemetry communication). It may be described that the device 10 may include a control module or controller, which may include the microprocessor 54 and memory 56.

The implantable device 10 further includes telemetry circuitry 64 and an antenna 65. Data and commands may be transmitted and received during uplink or downlink telemetry between the device 10 using the telemetry circuitry 64 and antenna 65 and the external monitoring device 50. In at least one embodiment, the wireless operable coupling between the device 10 and the external monitoring device 50 may use one or more wireless (e.g., radio frequency) data transmission protocols such as, e.g., BLUETOOTH, WI-FI, any protocol in the ultra high frequency (UHF) band, any protocol in the super high frequency (SHF) band, low frequencies, etc.

FIG. 3 is a functional block diagram of the exemplary external monitoring devices 20 shown in FIGS. 1A-1C. In one or more embodiments, the external monitoring device 20 may be located at home with a patient or with the patient at most, if not all, times, and used with the one or more implantable devices 10 implanted in the patient. Further, in at least one embodiment, the external monitoring device 20 is a cellular telephone. In one or more embodiments, the external monitoring device 20 may be located in a clinic or other medical facility and used for wirelessly communicating with multiple implantable devices 10 for multiple patients.

The external monitoring device 20 shown in FIG. 3 includes a telemetry circuit 72 and an antenna 73 for bidirectional communication with the implantable devices 10 shown in FIGS. 1A-1C. As described herein, data and commands may be transmitted and received during uplink or downlink telemetry between the device 10 using the telemetry circuitry 64 and antenna 65 and the external monitoring device 50 using the telemetry circuit 72 and the antenna 73. In at least one embodiment, the wireless operable coupling between the device 10 and the external monitoring device 50 may use one or more wireless (e.g., radio frequency) data transmission protocols such as, e.g., BLUETOOTH, WI-FI, any protocol in the ultra high frequency (UHF) band, any protocol in the super high frequency (SHF) band, low frequencies, etc.

The external monitoring device 20 may be described as being a microprocessor-controlled device, and thus, may include a microprocessor 74. The microprocessor 74 may operate with associated memory 78 for controlling various processes and functions of the external monitoring device 20 including initiating one or more measurements using the implantable devices 10, and wirelessly transferring data and commands between the implantable devices 10 and the external monitoring device 20. The microprocessor 74 may be further configured to store data from the implantable devices 10, calculate or determine various metrics or values such as, e.g., hemodynamic status, or index, values, pulse transit times, one or more fiducial points located within waveforms (e.g., electrocardiograms, impedance waveforms, acoustic signals, pressure signals, etc.), issue alerts or messages in view of various determinations, etc.

The memory 78 may be used alone or in combination with the memory 56 of the implantable devices 10 to store sensed data (e.g., impedance data, electrocardiogram data, pressure signals data, acoustic signal data, optical signal data, etc.) as well as information used in telemetry link control operations. Such telemetry link information may include conditions for verifying a telemetry session is active or inactive, time intervals for monitoring for such conditions, and messages that may be displayed during a telemetry termination operation.

In order for a person to interact with the external monitoring apparatus 20, the external monitoring apparatus 20 may include a user interface 71 coupled to microprocessor 74. The user interface 71 may include a touchscreen, a keyboard, graphical user interface, and/or combinations thereof. Further, the external monitoring apparatus 20 may include a display 76. The user interface 71 may allow a user to view and/or manipulate data on the display 76 and allow a user to interact with the implantable medical devices 10. The external monitoring apparatus 20 may further include a speaker 77 for broadcasting audible tones or messages used to communicate with a user regarding, e.g., a hemodynamic status of the user, alerts, alarms, etc.

The external monitoring apparatus 20 may further include a communications module 79 used for transferring data (e.g., over the internet, over a network, etc.) to a central database or communicating with other patient management systems such as the centralized system described herein with references to FIG. 16. The external monitoring apparatus 20 may further include an interface 75 for coupling peripheral devices which may include external monitoring equipment such as electrocardiogram leads, blood pressure monitor, etc.

A flow diagram of an exemplary method 40 of monitoring aggregate hemodynamic status of a patient using, e.g., the systems and devices of FIGS. 1-3, is depicted in FIG. 4. The exemplary method 40 may include measuring a first signal from tissue of a patient and a second signal from tissue of the patient 41. The first and second signals may be measured from tissue of the patient in different locations. More specifically, one of the first and second signals may be measured in a location further along a circulatory path from the patient's heart than the other location where the other signal is measured such that the signals may be used to determine a pulse transit time. In one or more embodiments, one of the first and second signals may be measured in a location physically further away from the patient's heart than the other location where the other signal is measured. It is to be understood that implantable device(s) may be initiated to perform the signal measurements from an external monitoring device and/or may be self-initiated to perform the signal measurements (e.g., the implantable device(s) may not need to be initiated to perform signal measurements from another device). The exemplary method 40 will be further described herein with respect to the exemplary system 5 depicted in FIG. 5A.

Figure 5A:
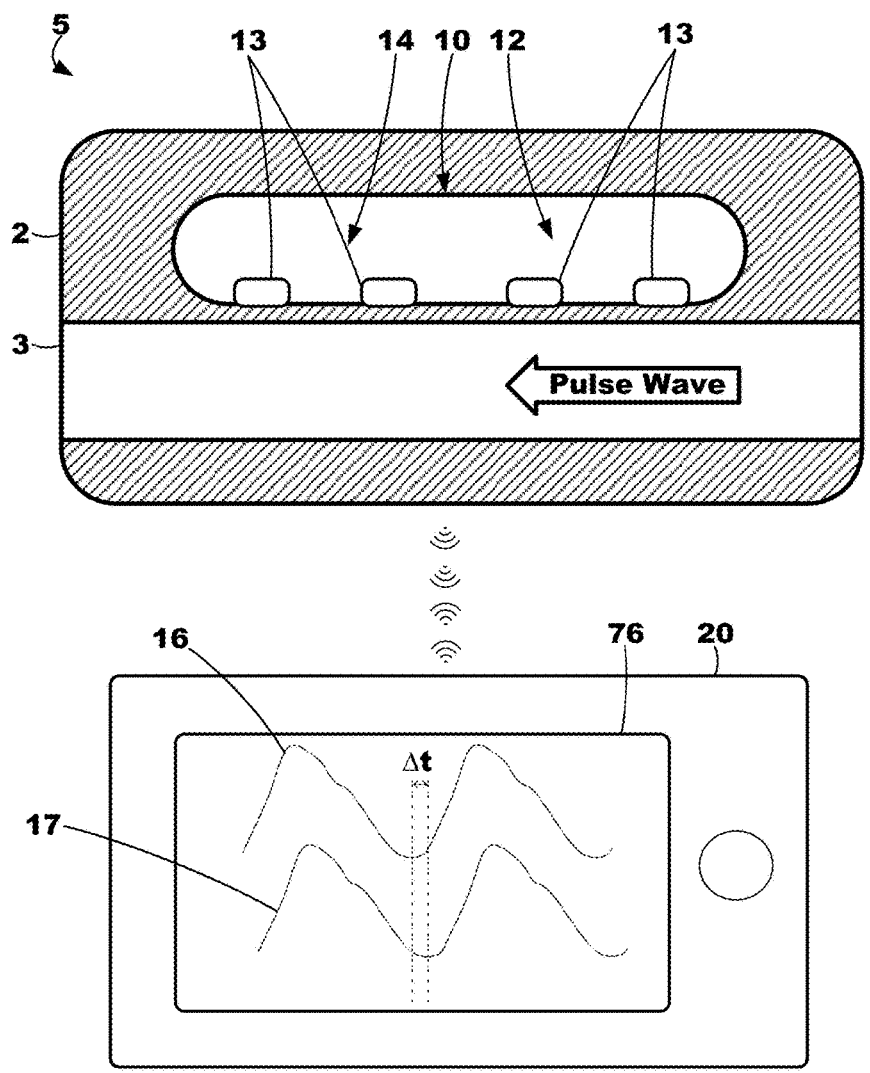
FIGS. 5A-5B depict exemplary systems for monitoring hemodynamic status of a patient including a single implantable device having two sensors.

An exemplary system 5 for monitoring hemodynamic status of a patient including a single implantable device 10 is shown in FIG. 5A. The device 10 of FIG. 5A is shown implanted in tissue 2 of a patient proximate an artery 3. The device 10 includes a first sensor 12 configured to measure a first signal from tissue 2 proximate the artery 3 and a second sensor 14 configured to measure a second signal from tissue 2 proximate the artery 3 that is located further along a circulator path from the patient's heart than where the first sensor 12 is measuring the first signal.

Each of the first and second sensors 12, 14 may include a pair of electrodes 13. The pair of electrodes 13 may be used to monitor various different types of signals with the tissue 2 proximate artery 3. For example, the electrodes 13 may measure impedance signals, electrocardiogram signals, and/or any electrical signal associated with a physiological parameter. In other exemplary devices 10, the first and second sensors 12, 14 may include, or use, other sensing apparatus other than electrodes such as optical sensors, pressure sensors, acoustic sensors, accelerometers, flow sensors, blood chemistry sensors, activity sensors, posture sensors, respiration sensors, etc. Regardless of the sensing modality, the first and second sensors 12, 14 may sense and generate a first and second signal, respectively, that includes a natural pulse originating from the heart or an artificial pulse originating from a pulse generator than traverses the patient's tissue, blood vessel structure, etc. Further, as shown, the second sensor 14 measures the second electrical signal in a location further along a circulatory path from the patient's heart than the where the first sensor 12 measures the first electrical signal.

The exemplary method 40 may transmit and receive data 42 representative of the first and second signals measured using the first and second sensors 12, 14 of the device 10. More specifically, data representative of the first and second signals may be transmitted from the implantable device 10 to the external monitoring device 20. For example, as shown in the exemplary system 5 of FIG. 5A, the first signal 16 and the second signal 17 have been transmitted to the external monitoring device 20 and are now displayed on the display 76 of the external monitoring device 20. It is to be understood that the first and second signals 14, 16 may not be displayed on the display 76 on the external monitoring device 20 during general usage of the system 5 and is shown in the examples of FIGS. 5-6 for explanatory purposes. Nonetheless, the signals 16, 17 could be displayed on the display 76 of the external monitoring device 20 is a user desired to do so (e.g., through some user interaction).

In other words, exemplary systems and processes to measure a timing interval from a single device are shown in FIG. 5A. A first signal 16 may be sensed from the first sensor 12 and either a digital representation of the first signal 16 or a time stamp corresponding to a fiducial point of the first signal 16 may be sent via a remote communication pathway to the external monitoring device 20 (e.g., a cell phone). The second signal 17 may be sensed by, or from, the second sensor 14 on the same device 10, and either a digital representation of the second signal 17 or a time stamp corresponding to a fiducial point of the second signal 17 may be sent via a remote communication pathway to the external monitoring device 20 (e.g., a cell phone). A pulse transit time calculation may be derived from the difference in time between fiducial points in the two signals 16, 17 and/or two time stamps/markers. Additionally, in one or more embodiments, single device calculations, such as pulse transit time calculations, can also be used in place of transmitting data representative of the first and second signals 16, 17 to the external monitoring device 20, and subsequently, the pulse transit times can be transmitted to the external monitoring device 20.

It is described that the data representative of the first and second signals 16, 17 is transmitted from the implantable medical device 10 to the external monitoring device 20 because, at least in some embodiments, the actual signals themselves may not be transmitted to the external monitoring device 20. Instead, for example, a digital representation of the signals 16, 17 may be transmitted to the external monitoring device. More specifically, the first and second signals 16, 17 may be sampled a particular sampling rate, or frequency, and the data points representative of the signals 16, 17 may be the data that is transferred to the external monitoring apparatus 20. Further, for example, a time stamp corresponding to a particular fiducial point along the first and second signals 16, 17 may be transferred to the external monitoring apparatus 20. Regardless, the data representative of the first and second signals 16, 17 is such that the external monitoring apparatus is capable to determine, or calculate, a pulse transit time therefrom.

Additional system configurations including a single implantable device 10 or two implantable devices 10 using a variety of different sensors are depicted in FIGS. 5-6. It is to be understood the configurations depicted in FIGS. 5-6 do not represent or depict all of the configurations that are be considered by this disclosure. Instead, the system configurations depicted in FIGS. 5-6 are merely a few examples.

Figure 5B:
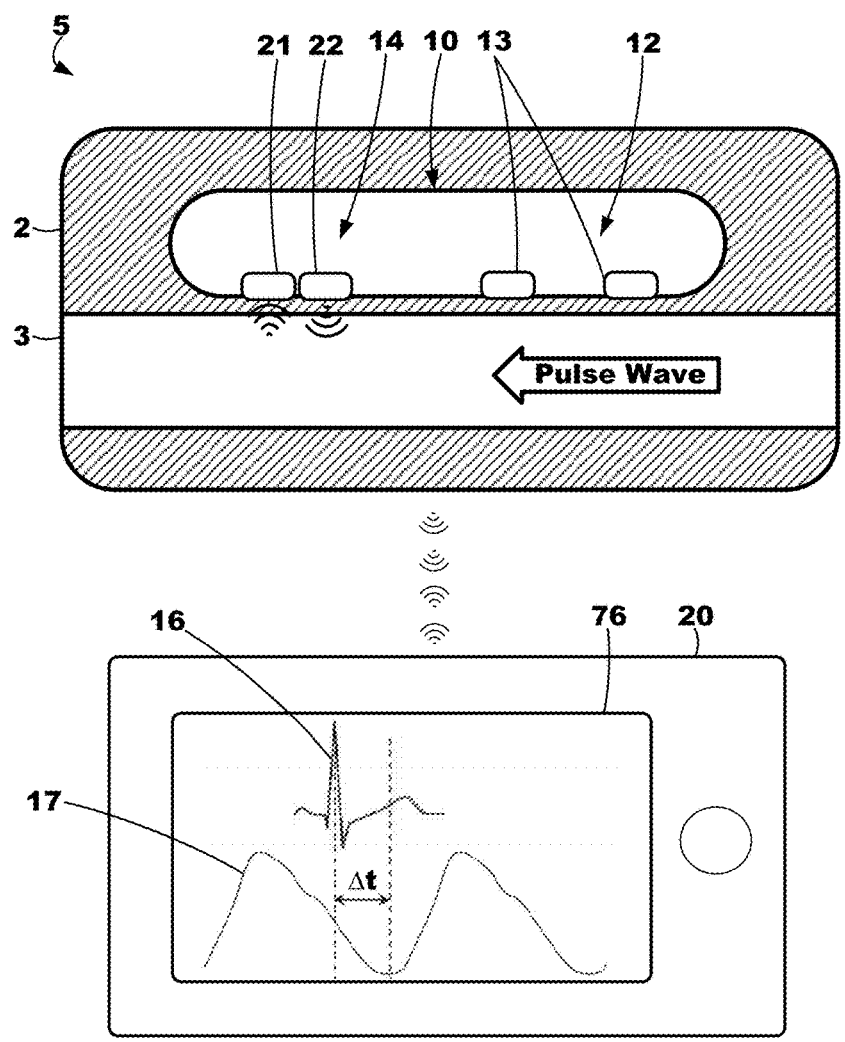

The exemplary system 5 of FIG. 5B is similar to the system 5 of FIG. 5A. For example, the system 5 of FIG. 5B includes a single implantable device 10 that has a pair of sensors 12, 14 and an external monitoring device 20. In this system 5 of FIG. 5B, however, the first sensor 12 is an electrocardiography sensor including a pair of electrodes 13 for measuring an electrocardiography signal and the second sensor 14 is an optical sensor including a light emitter 21 and a light detector 22 for measuring an arterial pulse waveform. As shown, the second sensor 14 measures the arterial pulse waveform in a location further along a circulatory path from the patient's heart than the where the first sensor 12 measures the electrocardiography signal. The first signal 16, which is an electrocardiogram signal, and the second signal 17, which is an optically-acquired arterial pulse waveform, are displayed on the display 76 of the external monitoring device 20. As shown, a pulse transit time may be measured between the peak of the R-wave in the first signal 16 to the minimum value in the second signal 17.

The systems 5 of FIGS. 5A-B may rely, or use, the heart's native impulse that may be too weak to be detected in large and small veins. The systems 5 of FIGS. 5C-5D may extend the exemplary methods and devices from measurement of arterial tissue to the measurement of venous tissue (e.g., the stiffness/compliance of venous tissue). The addition of venous measurements may assist clinician in determining which types of medication intervention is most suitable for the patient such as, e.g., diuretics or nitrates.

Figure 5C:
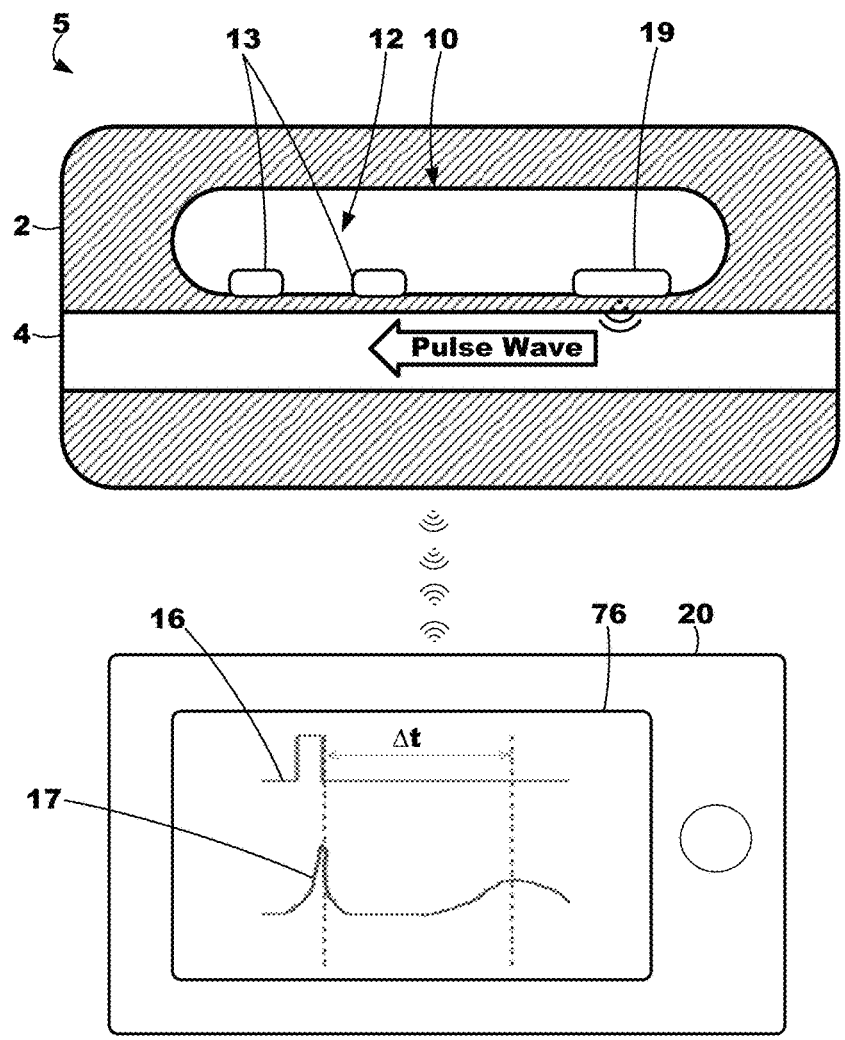

Since the heart's native impulse may be too weak to sense in venous tissue (and in some arterial tissue), the device 10 of FIG. 5C may include a pulse generator, or activator, 19 (e.g., the pulse delivery module 50) configured to generate a pressure wave within the vein 4 of the tissue 2. A time stamp may be associated with the delivery of the pressure wave, which may be used as the first signal 16. As shown in the display 76 of the monitoring device 20, the time stamp is represented by a square wave within the first signal 16. In at least one embodiment, the pulse generator 19 may include a piezoelectric crystal configured to generate and deliver the pressure wave within the venous tissue. In other embodiments, the pulse generator 19 may be configured to deliver pulses such as, e.g., electrical pulses (e.g., to contract tissue to cause a pressure pulse within a blood vessel or vasculature, etc.), pressure pulses, acoustic pulses, ultrasound pulses, etc., to a patient's tissue. Generally, the pulse generator 19 may be described as being configured to deliver, or initiate, mechanical, or physical, pulses to a patient's blood vessel (e.g., an artery or a vein).

The first sensor 12 of the device 10 of FIG. 5C may include a pair of electrodes to measure the second signal 17, which in this embodiment, is an impedance waveform. As shown, the sensor 12 measures the second signal 17 in a location further along a circulatory path from the patient's heart than the where pulse generator, or activator, 19 delivers a pressure wave or pulse. A pulse transit time may be calculated by the monitoring apparatus 20 between the square wave of the first signal 16 and a fiducial point representative of the propagated pulse within the second signal 17. Please note that the first peak in the second signal 17 may be a stimulus pulse artifact from the activator.

Additionally, the system 5 of FIG. 5C can also be used to measure pulse transit time within venous and arterial tissue such as shown in FIG. 5D. The device 5 of FIG. 5D is substantially similar to the device 5 of FIG. 5C except that the device 5 is located proximate both a vein 2 and an artery 3. In this embodiment, the second signal 17 includes a propagated arterial pulse and a propagated venous pulse. As shown, the propagated arterial pulse is faster than the propagated venous pulse, and an arterial pulse transit time, $\Delta t1$, and a venous pulse transit time, $\Delta t2$, may be calculated using the same signals 16, 17. Again, as before the first peak in the second signal 17 may be a stimulus pulse artifact.

Figure 6A:
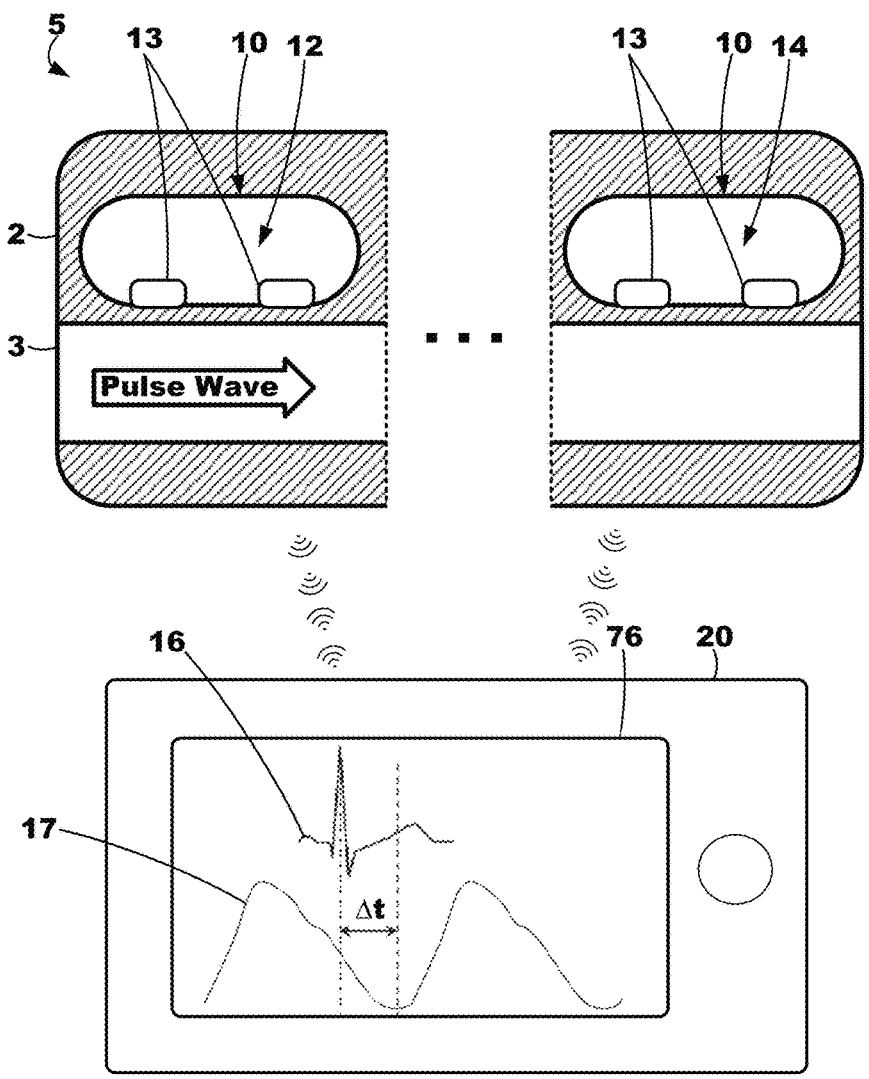

Exemplary systems 5 for monitoring hemodynamic status of a patient including two implantable devices 10 are depicted in FIGS. 6A-6C. As described herein, one of the implantable devices 10 may be located (e.g., implanted subcutaneously, implanted paravascular, etc.) closer to the patient's heart along a circulatory path than the other implantable device. In at least one embodiment, one of the implantable devices 10 may be located physically closer to the patient's heart than the other implantable device. As shown in the examples of FIGS. 6A-6C, the implantable device 10 located on the left side of the figures is located closer to the patient's heart along the circulatory path than the implantable device 10 located on the right side. Each of the devices 10 of FIGS. 6A-6C include a pair of electrodes 13 configured to measure an impedance waveform and/or an electrocardiogram signal. Further, each of the device 10 of FIGS. 6A-6C may be wirelessly operably coupled to at least the external monitoring apparatus 20 for data transfer therebetween and may be wirelessly operably coupled to each other for data transfer therebetween.

In FIG. 6A, the first signal 16 measured by the first sensor 12 of the first device 10 is an electrocardiogram signal and the second signal 17 measured by the second sensor 14 of the second device 10 is an impedance signal. As shown, the second sensor 14 measures the second signal 17 in a location further along a circulatory path from the patient's heart than the where the first sensor 12 measures the first signal 16. As before, a pulse transit time, Δt, may be determined between the peak of the R-wave of the first signal 16 and the minimum of the second signal 17. In other words, FIG. 6A depicts exemplary systems and processes to measure a timing interval from a plurality of devices 10. A sensed ECG R-wave signal and/or a corresponding time stamp may be transmitted, or sent, from a primary device 10 via a remote communication pathway to the external monitoring device 20 (e.g., cell phone). A signal from a distal secondary device 10 may be subsequently sensed, and the signal and/or a corresponding time stamp of this sensed signal may also sent via a remote communication pathway to the external monitoring device 20. A pulse transit time calculation may be derived from the difference in time between the two fiducial points in the signals 16, 17 and/or time stamps/markers related thereto. In at least one embodiment, intrabody communication between the two devices 10 can also be used in place of remote device telemetry.

In FIG. 6B, the first sensor 12 of the first device 10 may be measure an electrocardiogram signal, an impedance signal, and/or any other signal indicative of a pressure pulse, and then the first device 10 may transmit a time stamp represented by a square wave of in the first signal 16 corresponding to a fiducial point within with the measured signal to the external monitoring device 20. In another embodiment (not depicted), the first device 10 may transit a pulse (e.g., electrical pulse, pressure pulse, etc.) into the blood vessel tissue (e.g., into the artery), and subsequently, transmit a time stamp represented by a square wave in the first signal 16 corresponding to the moment when the pulse was transmitted into the blood vessel tissue to the external monitoring device 20. As shown, the second signal 17 measured by the second sensor 14 of the second device 10 is an impedance signal. Further, the second sensor 14 measures the second signal 17 in a location further along a circulatory path from the patient's heart than the where the first sensor 12 measures the first signal 16. As before, a pulse transit time, Δt, may be determined between the square wave of the first signal 16 and the minimum of the second signal 17.

In other words, FIG. 6B depicts exemplary systems and processes to measure a timing interval from a plurality of devices 10. A cardiac event may be sensed by a primary device 10 using sensor 12, and a corresponding time stamp of this event may be sent via a remote communication pathway to the external monitoring device 10 (e.g., a cell phone). Or, a pulsed signal may be administered secondary to a sensed cardiac event from the primary device 10 and a corresponding time stamp of this pulsed signal may be sent via a remote communication pathway to the external monitoring device 10. A signal from a distal secondary device 10 (or plurality of devices 10) may be subsequently sensed, and data representative of the second signal 17 (e.g., a digital representation of the second signal 17, a corresponding time stamp of this signal 17) may also sent via a remote communication pathway to the external monitoring device 20. A pulse transit time calculation may be derived from the difference in time between the time stamp of the first signal 16 (e.g., the square wave) and either a fiducial point within the second signal 17 or a time stamp from the second sensor 14.

In FIG. 6C, the first signal 16 measured by the first sensor 12 of the first device 10 is an impedance signal and the second signal 17 measured by the second sensor 14 of the second device 10 is also an impedance signal. As shown, the second sensor 14 measures the second signal 17 in a location further along a circulatory path from the patient's heart than the where the first sensor 12 measures the first signal 16. Each signal 16, 17 may be transmitted, or delivered, to the external monitoring device 20. As before, a pulse transit time, Δt, may be determined between the minimum value of the first signal 16 and the minimum value of the second signal 17 as depicted on display 76 of the external monitoring device 20.

Thus, the exemplary method 40 may further include determining a pulse transit time 43 based on the data representative of the first and second signals 16, 17. In one or more embodiments, the pulse transit time may be calculated by measuring the time between a selected fiducial point in the first signal 16 and a selected fiducial point in the second signal 17. An exemplary arterial waveform over time including a plurality of selected fiducial points is depicted in FIG. 7.

Potential arterial waveform parameters for identifying one or more fiducial points are depicted about the arterial waveform 91 of FIG. 7 that may be used for pulse transit time determination, which may be used to assess the hemodynamic status of a patient. For example, the minimum value (A) indicative of minimum vessel distention associated with diastole and the maximum value (B) indicative of maximum vessel distention associated with systole may be used as fiducial points. As shown, the time between the minimum values (A) may provide cardiac cycle time (C). Further, for example, the maximum slope (D) indicative of the maximum rate of vessel distention and the minimum slope (E) indicate of the minimum rate of vessel relaxation may also be used as fiducial points.

The exemplary fiducial points identified in FIG. 7 may be used to determine a pulse transit time by identifying a selected fiducial point on the first signal 16, identifying a selected fiducial point on the second signal 17, and calculating, or determining, the time between the two fiducial points occurring. For example, as shown in FIG. 5A, the selected fiducial points for each of the first and second signals 16, 17 are the minimum values. The time between the minimum value of the first signal 16 and the minimum value of the second signal 17, Δt, may be used as the pulse transit time.

As described herein, the data representative of the first signal 16 may be a digital representation of the first signal 16 or a time stamp, and likewise, the data representative of the second signal 17 may be a digital representation of the second signal 17 or a time stamp. It is to be understood that a time stamp is essentially the time at which a selected fiducial point occurs within a waveform or signal. Thus, the implantable device 10 may be performing the fiducial point analysis in these examples where a time stamp is transmitted to the external monitoring device 20. The external monitoring device 20 may calculate the pulse transit time using one or more time stamps. For example, in at least one embodiment, the data representative of the first signal 16 may be a time stamp while the data representative of the second signal 17 may be a digital representative of the second signal 17. Thus, in this embodiment, a fiducial point may be determined in the second signal 17, and the fiducial time stamp (i.e., the time at which the fiducial point occurs) may be used with the time stamp of the first signal 16 to determine the pulse transit time. Further, for example, in at least another embodiment, the data representative of the first signal 16 may be a time stamp and the data representative of the second signal 17 may be a time stamp. In this embodiment, the time between the two time stamps may be the pulse transit time.

In at least another embodiment, the implantable device 10 may calculate the pulse transit time by comparing time stamps from fiducial points that the device 10 itself determined, or calculated, in this first and second signals 16, 17. In this example, the implantable device 10 may transmit the pulse transit time to the external monitoring device 20.

The first and second signals 16, 17 may be measured 41 and transmitted/received 42, and pulse transit times may be determined 43 over the course of a monitoring time period. Generally, the monitoring time period is selected to be a time period that is useful for assessment of the chronic hemodynamic health of a patient (as opposed to an acute measurement). As will described further herein, hemodynamic status values (e.g., daily surrogate hemodynamic status values, weekly surrogate hemodynamic status values, nighttime surrogate hemodynamic status values, daytime surrogate hemodynamic status values, etc.) will be generated based on the pulse transit times determined over the monitoring time period. In other words, the monitoring time period may provide hemodynamic status values that may be described as being aggregate values over a time period so as to be able to assess the chronic hemodynamic health of the patient.

In one or more embodiments, the monitoring time period is about 5 minutes to about 2 months. For example, the monitoring time period may be greater than or equal to about 5 minutes, greater than or equal to about 7 minutes, greater than or equal to about 10 minutes, greater than or equal to about 12 minutes, greater than or equal to about 15 minutes, greater than or equal to about 20 minutes, greater than or equal to about 25 minutes, greater than or equal to about 30 minutes, greater than or equal to about 45 minutes, greater than or equal to about 1 hour, greater than or equal to about 2 hours, greater than or equal to about 4 hours, greater than or equal to about 6 hours, greater than or equal to about 8 hours, greater than or equal to about 10 hours, greater than or equal to about 12 hours, greater than or equal to about 14 hours, greater than or equal to about 16 hours, greater than or equal to about 18 hours, greater than or equal to about 20 hours, greater than or equal to about 22 hours, greater than or equal to about 1 day, greater than or equal to about 2 days, greater than or equal to about 1 week, greater than or equal to about 2 weeks, greater than or equal to about 3 weeks, etc. and/or less than or equal to about 17 minutes, less than or equal to about 27 minutes, less than or equal to about 40 minutes, less than or equal to about 50 minutes, less than or equal to about 1.5 hours, less than or equal to about 3 hours, less than or equal to about 5 hours, less than or equal to about 7 hours, less than or equal to about 9 hours, less than or equal to about 11 hours, less than or equal to about 13 hours, less than or equal to about 15 hours, less than or equal to about 17 hours, less than or equal to about 19 hours, less than or equal to about 21 hours, less than or equal to about 23 hours, less than or equal to about 25 hours, less than or equal to about 1.5 weeks, less than or equal to about 2.5 weeks, less than or equal to about 3.5 weeks, less than or equal to about 1 month, less than or equal to about 2 months, etc. Further, as described further herein, in some embodiments, the monitoring time period may correspond to daytime and nighttime.

The first and second signals 16, 17 may be measured 41 and transmitted/received 42, and pulse transit times may be determined 43 over the course of a monitoring time period in a periodic fashion until the monitoring time period expires 44 as indicated by the arrow from process box 44 to process box 41. In other words, if the monitoring time period has not expired, the method 40 may loop back to measuring 41 first and second signals 16, 17, transmitting/receiving 42, and determining the pulse transit times 43. This measurement 41, transmission/reception 42, and pulse transit time determination 43 may occur periodically over the monitoring time period. For example, these processes 41, 42, 43 may occur about every 5 seconds to about every 60 seconds, and this period of time may be referred to as a monitoring time period. In one or more embodiments, the monitoring time period may be greater than or equal to about 5 seconds, greater than or equal to about 10 seconds, greater than or equal to about 20 seconds, greater than or equal to about 30 seconds, greater than or equal to about 60 seconds, greater than or equal to about 120 seconds, greater than or equal to about 5 minutes, greater than or equal to about 10 minute, greater than or equal to about 20 minutes, greater than or equal to about 30 minutes seconds, etc. and/or less than or equal to about 60 minutes, less than or equal to about 45 minutes, less than or equal to about 35 minutes, less than or equal to about 25 minutes, less than or equal to about 15 minutes, less than or equal to about 8 minutes, less than or equal to about 3 minutes, less than or equal to about 100 seconds, less than or equal to about 75 seconds, less than or equal to about 45 seconds, less than or equal to about 35 seconds, less than or equal to about 25 seconds, less than or equal to about 15 seconds, etc. Additionally, it is to be understood that the transmission/reception and pulse transit time determination processes 42, 43 may not occur every time a measurement process 41 occurs, and instead, the data from the measurement processes 41 may be transmitted/received 42 periodically over multiple monitoring time periods.

If the monitoring time period has expired, the method 40 may progress to determining a surrogate hemodynamic status value 45 (for the monitoring time period from the pulse transit times calculated during the monitoring time period). As described herein, a hemodynamic status value may be indicative of the hemodynamic health, or status, of a patient. Further, the hemodynamic status value may be described as an aggregate value because the hemodynamic status value represents, or is derived from, a plurality of pulse transit times over the monitoring time period. In other words, the hemodynamic status value represents a period of time, i.e., the monitoring time period, as opposed to an individual point in time.

Before converting the pulse transit times to a surrogate hemodynamic status value, one or more processes may be performed on the plurality of pulse transit times for the monitoring time period. For example, the plurality of pulse transit times may be averaged to provide a mean pulse transit time value. Further, additional processes that may be performed on the plurality of pulse transit times for the monitoring time period may include one or more of generating a median, generating a mode, filtering, generating ranges, removing outliers, generating standard deviations, etc.

A plurality of graphs showing how a plurality of pulse transit times may be converted into a surrogate hemodynamic status values and plotted over time are depicted in FIG. 8. As shown, for each day, a plurality of pulse transit time times 95 are plotted and an average pulse transit time 96 is calculated. A linear regression equation as plotted by line 97 may be used to convert the mean pulse transit time to a surrogate hemodynamic status value 98. Further, in one or more embodiments, the pulse transit times may be calibrated with respect to blood pressure values (e.g., for generating linear regression equations for converting pulse transit times to hemodynamic status values) is described herein with respect to the FIGS. 10-12. The surrogate hemodynamic status values 98 may be plotted over time as shown in graph 99, which may be used to identify and assess trends in the patient's aggregate hemodynamic health.

Thus, using the exemplary processes depicted in FIG. 8, the exemplary method 40 may determine a hemodynamic status value 45 based on the plurality of pulse transit times representative of the patient's aggregate hemodynamic status for the monitoring time period. In some embodiments, the hemodynamic status value may merely be the average, or other statistic, representative of the plurality of pulse transit times determined of the monitoring time period. Regardless of the mathematical operations or conversations, the hemodynamic status value may be representative of the plurality of pulse transit times measured during, or over, the monitoring time period and may be used, at least, to identify trends of multiple monitoring time periods that may be indicative of the patient's hemodynamic health. After determination of the hemodynamic status value, the hemodynamic status value may be stored 46 in memory, and the method 40 may continue for another monitoring time period as indicated by the arrow looping back to the measurement process 41.

The hemodynamic status value may be determined by one or both of the implantable devices 10 and the monitoring device 20. For example, the implantable devices 10 may determine the hemodynamic status value from the plurality of pulse transit times, and then transfer the hemodynamic status value to the monitoring device 20. Further, for example, the plurality of pulse transit times, or data thereof, may be transferred to the monitoring device 20, and the monitoring device 20 may determine, or calculate, the hemodynamic status value. In other words, step 45 may be performed by one or both of the implantable devices 10 and the monitoring device 20. Still further, the pulse transit times may be determined by the one or more devices 10 from the first and second signal data, and then transferred to the monitoring device 20. In sum, any of the one or more devices 10 and the external monitoring device 20 may perform any one or more of the steps described with reference to method 40.

Additionally, the method 40 may optionally be configured to compare the determined hemodynamic status value to a baseline or another metric, and issue an alarm to the patient 47. For example, the method 40 may determine from the trend of the hemodynamic status values that a patient's blood pressure has likely increased and needs medical attention, and thus, issue an alarm 47 to the external monitoring device 20. Further, for example, the method 40 may determine from the trend of the hemodynamic status values that a patient's blood pressure has likely increased and needs medical attention, and thus, may instruct the patient (e.g., through a message on the device 20) to perform a clinical action (e.g., take a medication), visit a clinician, go to an emergency room, etc. The external monitoring apparatus 20 may play a sound, display the alert, and/or vibrate to indicate to the user that an alarm and/or instruction is or has occurred.

Figure 9:
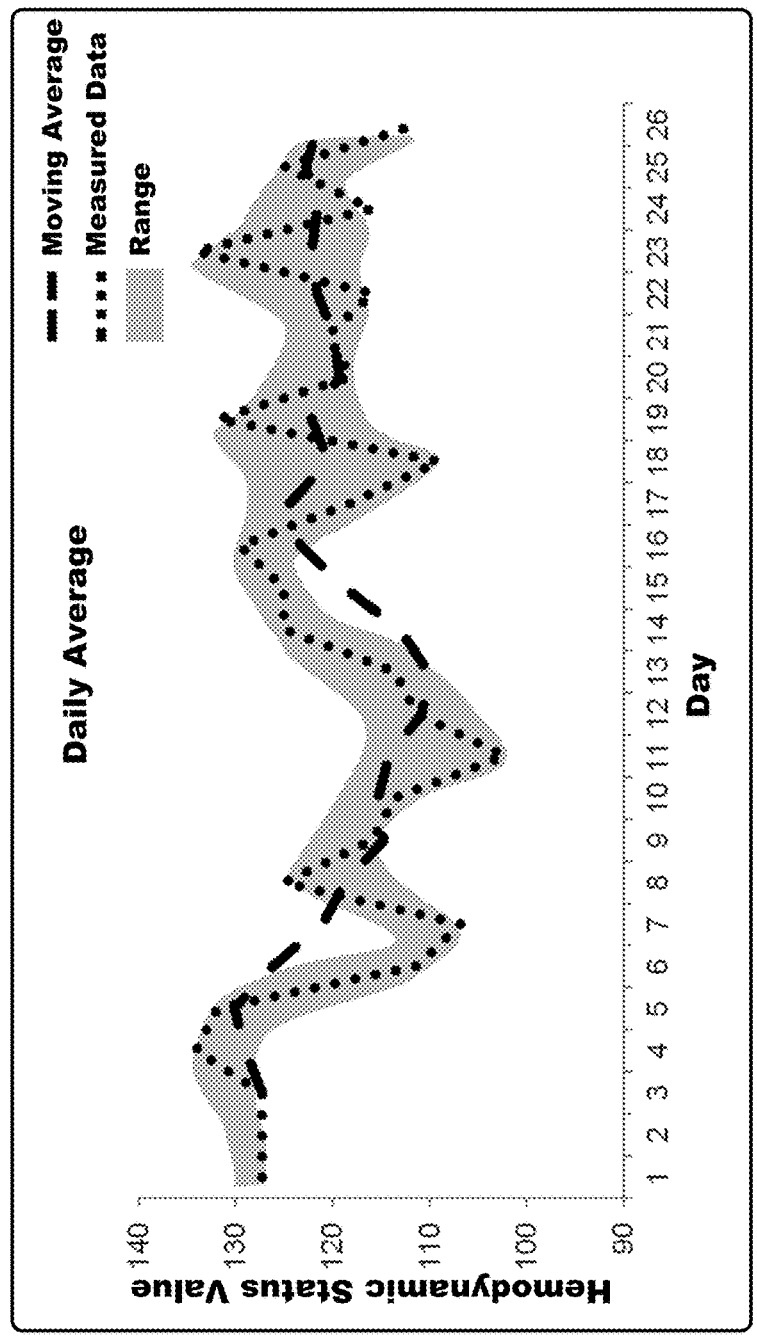
FIG. 9 is a graph of a surrogate hemodynamic status value over time.

Another graph of a surrogate hemodynamic status values plotted over time is depicted in FIG. 9. In this depiction, surrogate hemodynamic status values are displayed in multiple ways to provide additional information to a practitioner when identifying and assessing trends in the patient's hemodynamic health. More specifically, the actual surrogate hemodynamic status values, a moving average of the surrogate hemodynamic status values, and a range of the surrogate hemodynamic status values are plotted over time.

Figure 10:
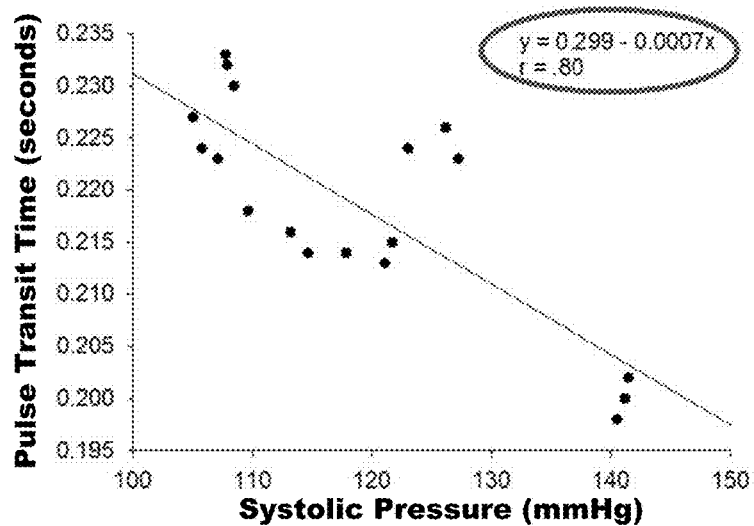
FIG. 10 is a graph of 24 hours of pulse transit time data versus systolic blood pressure measured during experimental testing for calibration.
Figure 11:
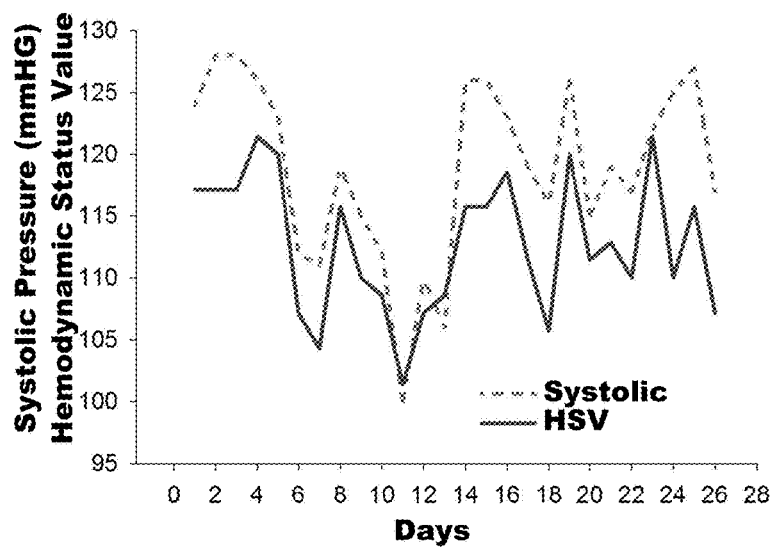
FIG. 11 is a graph of daily average actual systolic pressure and surrogate hemodynamic status values using the calibration data depicted in FIG. 10.
Figure 12:
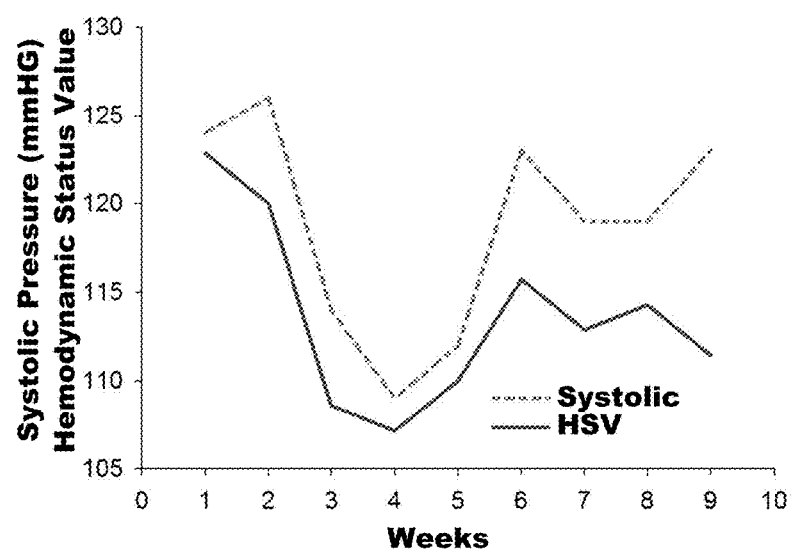
FIG. 12 is a graph of weekly actual average systolic pressure and surrogate hemodynamic status values using the calibration data depicted in FIG. 10.

A graph of 24 hours of pulse transit time data versus systolic blood pressure measured during experimental testing is shown in FIG. 10. From this data taken over 24 hours, a linear regression equation was fitted to the data, which is y=0.299–0.0007x with an r-value of 0.80. A graph of daily actual systolic pressure and surrogate hemodynamic status value using the linear regression equation from the data depicted in FIG. 10 is shown in FIG. 11. As shown, the surrogate hemodynamic status values relatively closely tracked the actual systolic data over the 26 days. In this example, each daily surrogate hemodynamic status value plotted in FIG. 11 was generated by measuring pulse transit time for each heart beat for 10 minutes each hour of the day. Three pulse transit times were selected from each 10 minute period (e.g., as being representative of the 10 minute period), and the selected pulse transit times from each 10 minute period for the entire day were then averaged to generate the surrogate hemodynamic status value for the day. A graph of weekly actual systolic pressure and surrogate hemodynamic status value using the linear regression equation from the data depicted in FIG. 10 is shown in FIG. 12. In this example, each weekly surrogate hemodynamic status value plotted in FIG. 12 was generated by averaging one week of daily surrogate hemodynamic status values. As shown, the surrogate hemodynamic status values relatively closely tracked the actual systolic data over the nine weeks.

Figure 13:
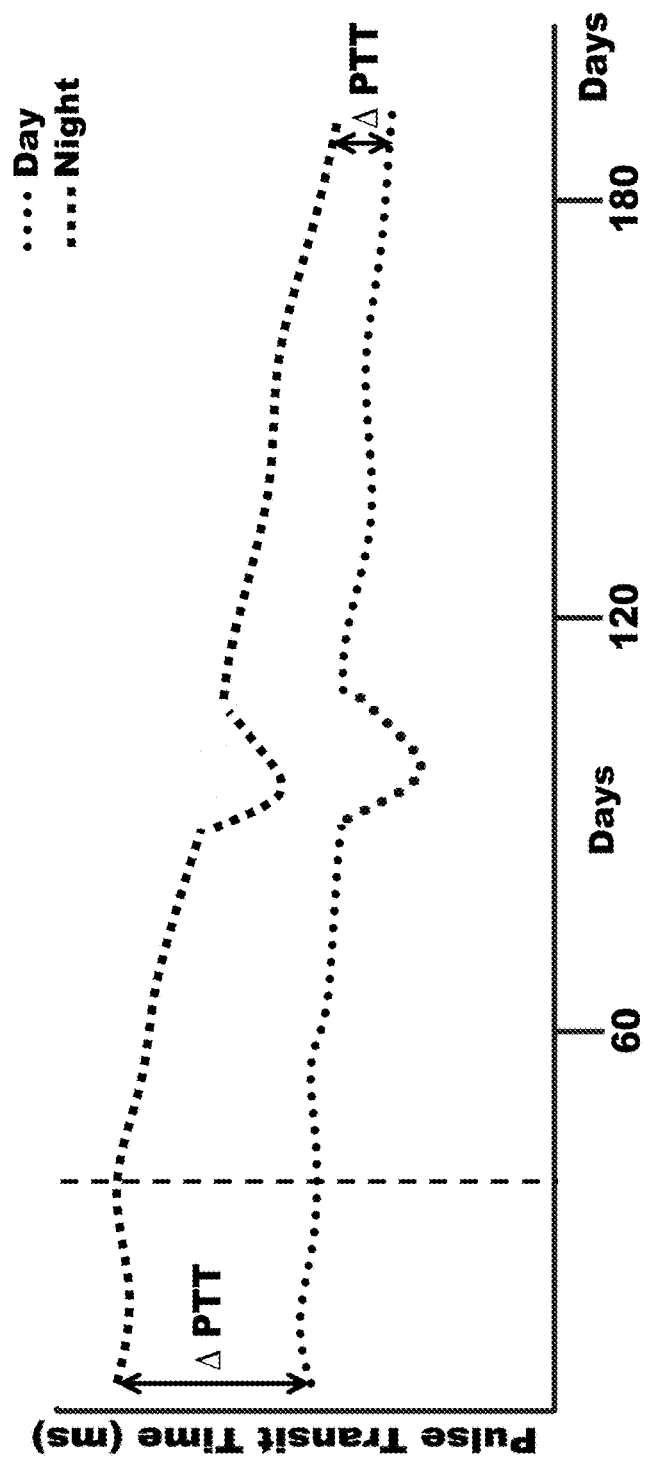
FIG. 13 is a graph of exemplary day and night pulse transit time data over time determined using, e.g., the exemplary systems and methods of FIGS. 1-6.

As described herein, the monitoring time period may include a portion of a day such as nighttime and daytime. The hemodynamic status values for daytime and nighttime may provide additional metrics or data that may be useful in assessing a patient's hemodynamic status. For example, a graph of exemplary daytime and nighttime pulse transit time data over time determined using, e.g., the systems and methods of FIGS. 1-6 is shown in FIG. 13. In this example, the monitoring time period included each nighttime and each daytime, and an average pulse transit time was calculated, or determined, for each nighttime and daytime. By plotting the daytime and nighttime average pulse transit times, the difference, or change between, the average pulse transit time for daytime and nighttime is visualized. This daytime/nighttime blood pressure change, as approximated by the daytime/nighttime pulse transit times, may be useful to detect patterns, which may be indicative of the patient's hemodynamic health. For example, as shown in this graph, the difference between daytime and nighttime pulse transit times are decreasing, which may indicate an overall blood pressure increase, a decrease in the patient's hemodynamic health, a change in medication (e.g., a change in type, dose, etc.) that the patient is taking, non-compliance with treatment options (e.g., failure to take medication, etc.), poor sleep, change in sleep patterns, stress, any other physiological changes, etc. Additionally, as shown in this graph, both the daytime and nighttime pulse transit time values dropped at around 100 days, which could indicate to a practitioner that an event occurred such as, e.g., an increase in sodium intake, etc.

Figure 14:
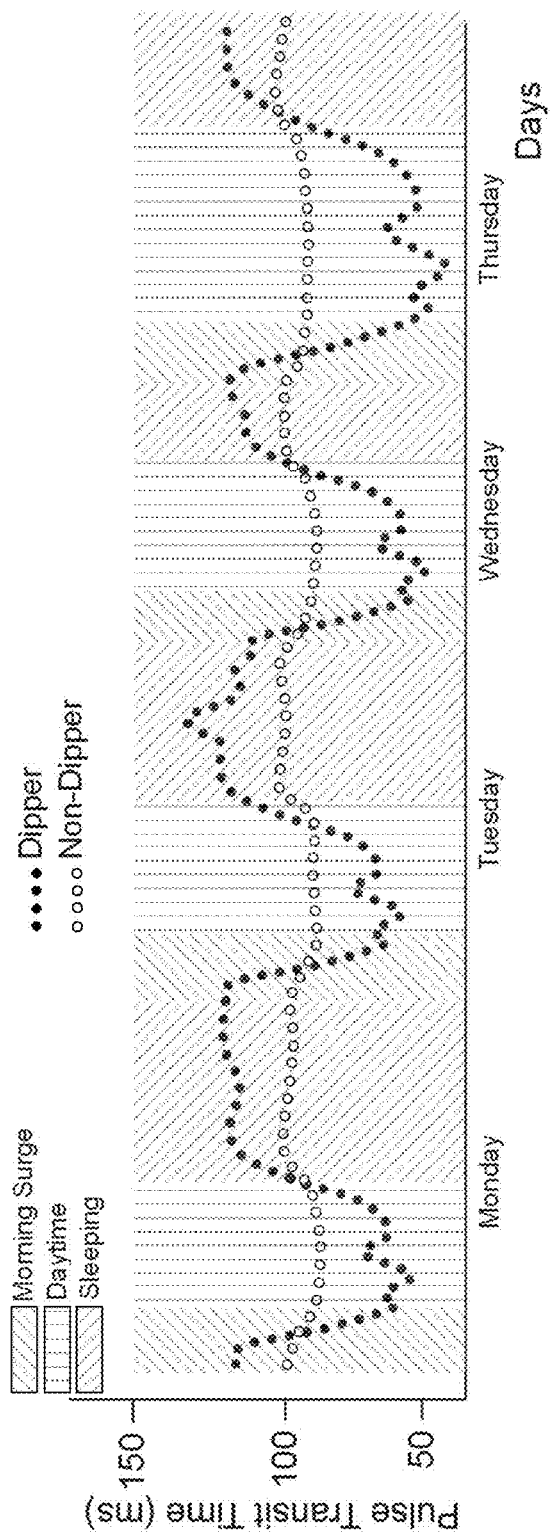
FIG. 14 is a graph of exemplary day and night pulse transit time data for "dipper" and "non-dipper" patients over time determined using, e.g., the exemplary systems and methods of FIGS. 1-6.

A graph of exemplary daytime and nighttime pulse transit time data for "dipper" and "non-dipper" patients over time determined using, e.g., the systems and methods of FIGS. 1-6 is shown in FIG. 14. For example, if a hemodynamic status values as derived from the pulse transit time data, does not decrease, or dip, 15% from daytime to nighttime, this lack of decrease may be indicative of a higher risk of cardiovascular disease.

A graph of exemplary change in surrogate hemodynamic status value over time determined using, e.g., the systems and methods of FIGS. 1-6 is shown in FIG. 15. This simplified graph may be an exemplary interface that is configured to be used by the patient and/or clinicians to view overall hemodynamic health trends without much clutter and unnecessary numerical data or complication. As shown, the simplified graph displays a percentage change in raised surrogate hemodynamic status value over time such that a user may easily ascertain increases or decreases in their general hemodynamic health.

The information obtained by the systems, devices, and methods described herein can be integrated into a centralized system 900 for remote monitoring and analysis, allowing easier use for the patient and caregivers as shown in FIG. 18. As described herein, pulse transit times or data representative of pulse transit times may be transmitted (e.g., transmitted wireless from) from one or more implantable devices 905 to an external monitoring device 906. The external monitoring device 906 can determine hemodynamic status values, which can then upload the hemodynamic status value data as well as pulse transit time data into the system 900. This data can then be stored with information from all data sources 901, including enrollment data 907, follow-up data 908, device and registrant tracking data 909, consumer data 910, and other data sources 911. The data can then be transferred to a data collection subsystem 902. This subsystem 902 can extract, transform and load the data 912, into a source warehouse 913. Copies of the data subsets 914 can be distributed by the data distribution subsystem 903, taking into account appropriate business rules 915 and privacy laws 916. This information can then be transferred to data marts 917. The data from the data marts 917 can then be transferred to a data analysis subsystem 904. The data analysis subsystem then makes data inferences 918, for each of the data marts to give the analyzable data 919, 920, 921. The data 919, 920, 921 can then be analyzed, including any analytics applications 925, to give analyzed information 922, 923, and 924. All of this can be done utilizing the data warehousing and analytics services components 926.

As described with respect FIGS. 8 and 10, a plurality of pulse transit times may be time correlated, or synchronized, to a plurality of blood pressure measurements, and a relationship, or function, such as, e.g., a linear regression, may be generated based on the plurality of pulse transit times and the plurality of blood pressure measurements. Such relationship may be used to convert a pulse transit time to an estimated blood pressure, and vice versa.

A change in the relationship between pulse transit time and blood pressure may also be useful in determining the hemodynamic status of a patient. For example, if the relationship between pulse transit time and blood pressure changes, it may indicate an overall blood pressure increase, a decrease in the patient's hemodynamic health, a change in medication (e.g., a change in type, dose, etc.) that the patient is taking, non-compliance with treatment options (e.g., failure to take medication, etc.), poor sleep, change in sleep patterns, stress, any other physiological changes, etc.

Pulse transit time data versus systolic blood pressure measured during a first and second time period is depicted in FIG. 17. In other words, a plurality of pulse transit times and systolic blood pressure values have been monitored over first and second time periods and such times and values have been plotted. As shown, a relationship 100, 102, or more specifically, a linear regression function, has been generated/modelled and plotted among the data points of pulse transit time versus systolic pressure for each of the first time period and the second time period. More specifically, a first line 100 has been plotted for the first time period and a second line 102 has been plotted for the second time period. In other words, a pulse transit time-blood pressure relationship 100, 102 has been generated between the pulse transit times and systolic blood pressure values for each time period.

As shown, the second line 102 is different, or has changed, from the first line 100, which may indicate that the hemodynamic status of a patient has changed (indicated by arrow 105). The exemplary methods and systems described herein may be configured to determine whether a hemodynamic status as changed based on a change in the pulse transit time-blood pressure relationship from the first time period to the second time period (e.g., over the first and second time periods). One numerical process to determine whether the relationship between pulse transit time and blood pressure has changed 105 may be to compare the slopes 101, 103 of the relationships to each other, and if the difference in slopes 101, 103 exceeds a threshold value, then the exemplary systems, methods, and devices described herein may determine that a significant hemodynamic status change has occurred.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in assessment of a patient's hemodynamic status comprising:
   one or more devices comprising:
      a first sensor to measure a first signal from tissue of a patient, and
      a second sensor to measure a second signal from tissue of the patient from a different location along a circulatory path from the patient's heart than the first sensor, wherein the one or more devices are configured to periodically measure the first and second signals over a monitoring time period; and
   an external monitoring device wirelessly operatively coupled to the one or more devices and configured to:
      receive data representative of the first and second signals from the one or more devices;
      determine a pulse transit time based on the data representative of the first and second signals for each measurement of the first and second signals resulting in a plurality of pulse transit times for the monitoring time period; and
      determine a surrogate hemodynamic status value based on the plurality of pulse transit times representative of the patient's aggregate hemodynamic status for the monitoring time period.

2. The system of claim 1, wherein the monitoring time period is greater than or equal to 1 hour.

3. The system of claim 1, wherein the external monitoring device is further configured to:
   monitor the hemodynamic status values for a plurality of monitoring time periods; and
   determine whether the hemodynamic status of the patient has changed based on the hemodynamic status values over the plurality of monitoring time periods.

4. The system of claim 3, wherein the external monitoring device is further configured to issue an alert if the hemodynamic status of the patient has changed based on the hemodynamic status values.

5. The system of claim 1, wherein the external monitoring device is further configured to:
receive a plurality of blood pressure values of the patient synchronized to the plurality of pulse transit times over the monitoring time period,
model a relationship between the plurality of blood pressure values and the plurality of pulse transit times;
monitor the relationship between the plurality of blood pressure values and the plurality of pulse transit times for at least two monitoring time periods; and
determine whether the hemodynamic status of the patient has changed based on a change in the relationship between the plurality of blood pressure values and the plurality of pulse transit times over the at least two monitoring time periods.

6. The system of claim 1, wherein the one or more devices comprises:
a first device comprising the first sensor; and
a second device comprising the second sensor.

7. The system of claim 1, wherein the one or more devices comprises a single implantable device comprising the first sensor and the second sensor.

8. The system of claim 1, wherein the one or more devices are subcutaneously implantable devices.

9. The system of claim 1, wherein the first signal comprises one or more of an electrocardiography signal and an impedance signal.

10. The system of claim 1, wherein the data representative of the first signal comprises a digital representation of one of an electrocardiography signal, an impedance signal, an acoustic signal, an optical signal, and an accelerometer signal.

11. The system of claim 1, wherein the data representative of the first signal comprises a time stamp corresponding to a fiducial point within one of an electrocardiography signal, an impedance signal, an optical signal, an acoustic signal, and an accelerometer signal.

12. The system of claim 1, wherein the second signal comprises one or more of an impedance signal, an optical signal, an acoustic signal, and an accelerometer signal.

13. A method for use in assessing a patient's hemodynamic status comprising:
periodically measuring a first signal from tissue of a patient and a second signal from tissue of the patient in a different location along a circulatory path from the patient's heart than where the first signal is measured over a monitoring time period;
receiving data representative of the first and second signals;
determining a pulse transit time based on the data representative of the first and second signals for each measurement of the first and second signals resulting in a plurality of pulse transit times for the monitoring time period; and
determining a hemodynamic status value based on the plurality of pulse transit times representative of the patient's aggregate hemodynamic status for the monitoring time period.

14. The method of claim 13, wherein the monitoring time period is greater than or equal to 1 hour.

15. The method of claim 13 further comprising:
monitoring the hemodynamic status values for a plurality of monitoring time periods; and
determining whether the hemodynamic status of the patient has changed based on the hemodynamic status values over the plurality of monitoring time periods.

16. The method of claim 15 further comprising issuing an alert if the hemodynamic status of the patient has changed based on the hemodynamic status values.

17. The method of claim 15 further comprising:
receiving a plurality of blood pressure values of the patient synchronized to the plurality of pulse transit times over the monitoring time period;
modelling a relationship between the plurality of blood pressure values and the plurality of pulse transit times;
monitoring the relationship between the plurality of blood pressure values and the plurality of pulse transit times for at least two monitoring time periods; and
determining whether the hemodynamic status of the patient has changed based on a change in the relationship between the plurality of blood pressure values and the plurality of pulse transit times over the at least two monitoring time periods.

18. The method of claim 13, wherein the first signal comprises one of an electrocardiography signal, an impedance signal, an optical signal, an acoustic signal, and an accelerometer signal.

19. The method of claim 13, wherein the data representative of the first signal comprises a digital representation of one of an electrocardiography signal, an impedance signal, an optical signal, an acoustic signal, and an accelerometer signal.

20. The method of claim 13, wherein the data representative of the first signal comprises a time stamp corresponding to a fiducial point within one of an electrocardiography signal, an impedance signal, an optical signal, an acoustic signal, and an accelerometer signal.

21. A system for use in assessment of a patient's hemodynamic status comprising:
one or more devices comprising:
a pulse generator to generate a pulse in tissue of a patient, and
a sensor to measure a signal from tissue of the patient from a different location along a circulatory path from the patient's heart than the pulse generator, wherein the one or more devices are configured to periodically deliver a pulse and measure the signal over a monitoring time period; and
an external monitoring device wirelessly operatively coupled to the one or more devices and configured to:
receive a time stamp corresponding to the delivery of the pulse and data representative of the signal from the one or more devices;
determine a pulse transit time based on the time stamp and the data representative of the signal for each pulse delivery and measurement of the signal resulting in a plurality of pulse transit times for the monitoring time period; and
determine a surrogate hemodynamic status value based on the plurality of pulse transit times representative of the patient's hemodynamic status for the monitoring time period.

* * * * *